United States Patent [19]

Rodríguez-Ubis et al.

[11] Patent Number: 5,859,215
[45] Date of Patent: Jan. 12, 1999

[54] BIOSPECIFIC BINDING REACTANTS LABELLED WITH LUMINESCENT LANTHANIDE CHELATES AND THEIR USE

[75] Inventors: Juan Carlos Rodríguez-Ubis, Madrid, Spain; Harri Takalo, Turku; Veli-Matti Mukkala, Kaarina, both of Finland

[73] Assignee: Wallac Oy, Turku, Finland

[21] Appl. No.: 548,174

[22] Filed: Oct. 25, 1995

[51] Int. Cl.[6] ............................. C07F 5/00; A61K 49/00; G01N 21/76; C07D 213/00
[52] U.S. Cl. ........................... 534/16; 424/9.36; 424/9.34; 424/9.6; 436/172; 546/2; 546/5; 546/6; 546/256
[58] Field of Search ........................ 534/16, 15; 424/1.65, 424/1.53, 1.69, 9.34, 9.361, 9.362, 9.6, 9.36, 9.364, 9.365; 436/504, 172; 540/465, 467, 470, 474; 546/2, 5, 6, 256, 323

[56] References Cited

U.S. PATENT DOCUMENTS

| | | | |
|---|---|---|---|
| 5,216,134 | 6/1993 | Mukkala et al. | 534/15 |
| 5,324,825 | 6/1994 | Kankare et al. | 534/16 |
| 5,346,996 | 9/1994 | Lehn et al. | 534/15 |
| 5,457,184 | 10/1995 | Lehn et al. | 534/15 |
| 5,457,186 | 10/1995 | Mukkala et al. | 534/15 |
| 5,559,214 | 9/1996 | Delecki et al. | 534/10 |
| 5,571,897 | 11/1996 | Takalo et al. | 534/15 |
| 5,583,206 | 12/1996 | Snow et al. | 534/16 |

FOREIGN PATENT DOCUMENTS

93/11433  6/1993  WIPO.

OTHER PUBLICATIONS

Abel et al., *J. Chem. Soc. Dalton Trans.*, (7) pp. 1079–1090, 1994.
Latva et al., *J. Chem. Perkin Trans. 2*, (5), pp. 995–999, 1995.
Modesto J. Remuiñán et al., "Synthesis and Luminiscence Properties of Europium (III) and Terbium (III) Complexes with Polyacid Chelates Derived from 2,6–Bis (N–pyrazolyl)pyridine", *J. Chem. Soc. Perkin Trans.*, 2, 1993, pp. 1099–1102.

Primary Examiner—José G. Dees
Assistant Examiner—Michael G. Hartley
Attorney, Agent, or Firm—Kubovcik & Kubovcik

[57] ABSTRACT

This invention relates to a detectable molecule comprising a biospecific binding reactant attached to a luminescent lanthanide chelate comprising a lanthanide ion and a chelating ligand of the formula

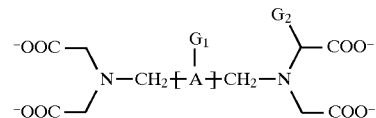

wherein —A— is a bivalent aromatic structure selected from the group consisting of

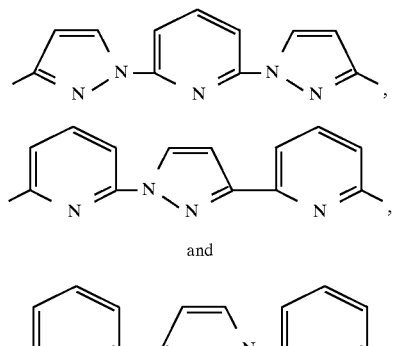

and One of the two groups $G_1$ or $G_2$ is used for coupling the chelate to a biospecific binding reactant. The lanthanide ion is europium(III), terbium(III), dysprosium (III) or samarium (III).

8 Claims, 1 Drawing Sheet

BIOSPECIFIC BINDING REACTANTS LABELLED WITH LUMINESCENT LANTHANIDE CHELATES AND THEIR USE

FIELD OF THE INVENTION

The present invention relates to detectables molecules comprising lanthanide chelates attached to a biospecific binding reactant and use of the said detectable molecules in bioaffinity based binding assays. The invention further relates to novel luminescent lanthanide chelates useful in the preparation of said detectable molecules.

BACKGROUND OF THE INVENTION

The publications and other materials used herein to illuminate the background of the invention, and in particular, cases to provide additional details respecting the practice, are incorporated by reference.

In specific binding assays, such as, e.g., immunoassays, DNA hybridization assays, receptor-binding assays, and cellular binding assays, generally the analytes to be measured are present at very low concentrations. Therefore, various labelling compounds have been developed that allow the labelled reactant to be detected and quantitated at high sensitivity. In immunoassays and DNA hybridization assays time-resolved luminescence spectroscopy using lanthanide chelates is well known (e.g., I. Hemmilä, T. Ståhlberg, and P. Mottram (eds.), "Bioanalytical Applications of Labelling Technologies", Wallac, Turku, 1994). Stable photoluminescent (referred in the context of this specification simply as luminescent) lanthanide chelates also have other applications, e.g. fluorescence microscopy and cytometry. Therefore, a number of attempts have been made to develop new highly luminescent chelate labels suitable for those types of time-resolved fluorometric applications. These include, e.g., stable chelates composed of derivatives of pyridines (U.S. Pat. No. 4,920,195, U.S. Pat. No. 4,801,722, U.S. Pat. No. 4,761,481, PCT WO FI-91/00373, U.S. patent application Ser. No. 08/135,525, now U.S. Pat. No. 5,459,186, Remuiñán, M. J., Román, H., Alonso, M. T. and Rodríguez-Ubis, J. C., 1993, J. Chem. Soc., Perkin Trans.2, 1099), bipyridines (U.S. Pat. No. 5,216,134), terpyridines (U.S. Pat. No. 4,859,777, U.S. Pat. No. 5,202,423, U.S. Pat. No. 5,234,825) or various phenolic compounds (U.S. Pat. No. 4,670,572, U.S. Pat. No. 4,794,191, Ital. Pat. 42508 A/89) as the energy mediating groups and polycarboxylic acids as chelating parts. In addition, various dicarboxylate derivatives (U.S. Pat. No. 5,032,677, U.S. Pat. No. 5,055,578, U.S. Pat. No. 4,772,563), macrocyclic cryptates (U.S. Pat. No. 4,927,923, PCT WO 93/5049, EP-A493,745) and macrocyclic Schiff bases (EP-A369,000) have been patented. None of these terbium chelates fulfill all the required features to be used as labels for bioaffinity assays. These requirements are high thermodynamic and kinetic chelate stability, hydrophilicity, high absorptivity at a suitable excitation wavelength, appropriate triplet state to enable efficient energy transfer, high luminescence intensity, presence of a functional group, allowing the formation of a covalent linkage between the chelate and the target molecule, and the retention of the affinity and nonspecific binding properties of the used biomolecules. In case of $Tb^{III}$, the energy gap between the excitation state of the donor ligand and the emitting level of the $Tb^{III}$ ion should be high enough to prevent energy back transfer (Sabbatini, N., Mecati, A., Guardigli, M., Balzani, V., Lehn, J.-M., Zeissel, R. and Ungaro, R., 1991, J. Luminescence 48 & 49; 463–468). Moreover, with exactly the same ligand structure, none of the labels made from the prior art chelates has enough high luminescence intensities with both $Eu^{III}$ and $Tb^{III}$. In some applications, which contain various chromatographic separation steps, it would be preferable that the label structures differ from each other only with respect to the lanthanide used. Besides, the same key intermediates can be used in the preparations of several lanthanide labels, e.g., $Eu^{III}$ and $Tb^{III}$ labels.

SUMMARY OF THE INVENTION

According to the present invention, the problem of $Tb^{III}$ chelate labels can be solved and the development of more luminescent $Tb^{III}$ chelates is made possible. By preparing suitable ligand structures the energy back transfer from the donor ligand to the emitting level of the $Tb^{III}$ ion, i.e., the excited state deactivation route, can be eliminated, and at the same time, all other important features of labels and labelled biomolecules can be retained.

One object of this invention is to provide a detectable molecule comprising a biospecific binding reactant attached to a luminescent lanthanide chelate according to this invention.

Another object of the present invention is to provide a luminescent lanthanide chelate.

Yet another object of the present invention is to provide the use of a detectable molecule comprising a biospecific binding reactant attached to the luminescent chelate according to this invention.

A further objective of this invention is to provide a chelating agent which has high luminescence intensity with several lanthanides, particularly with $Tb^{III}$ and $Eu^{III}$, with exactly the same chelating structure.

DETAILED DESCRIPTION OF THE INVENTION

Figure 1:
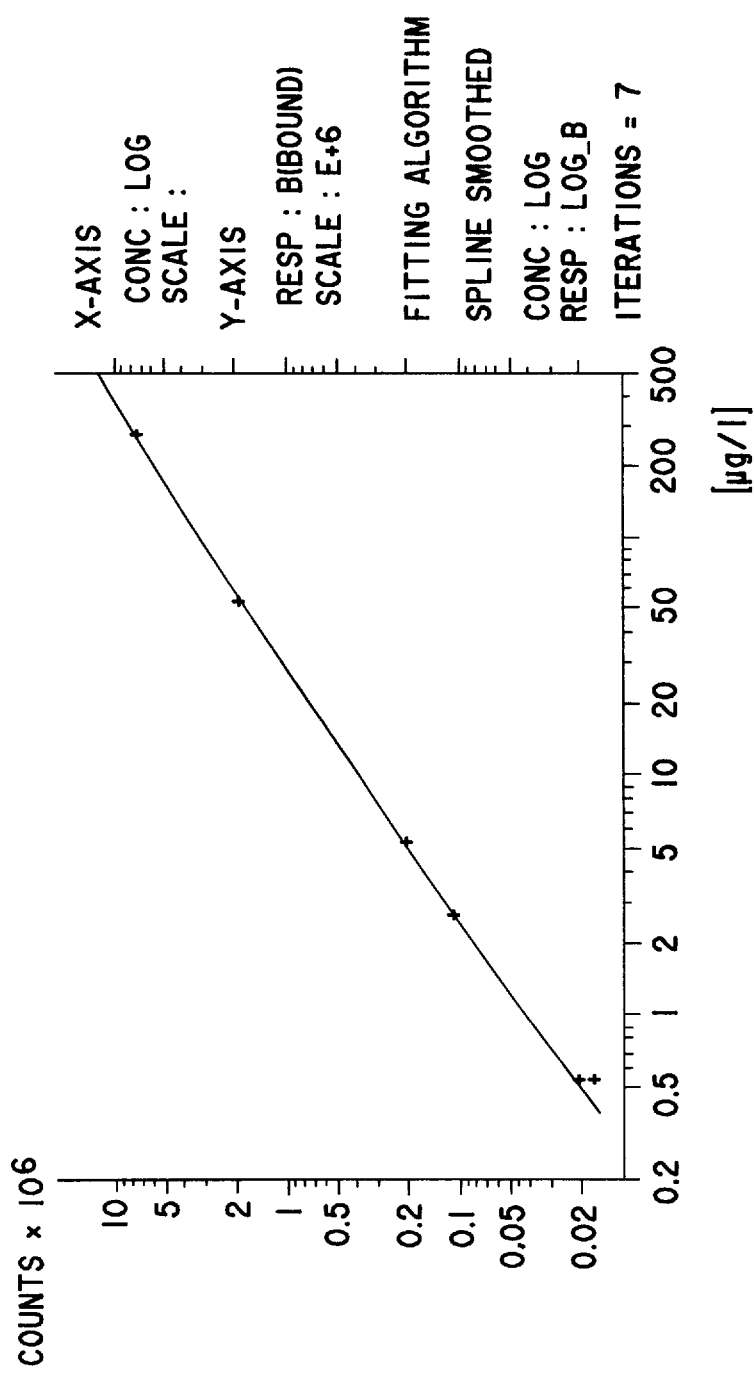
FIG. 1 illustrates a PSA standard curve wherein a PSA-antibody labeled with a terbium(III) chelate of the present invention is used as a label.

The aim of the present invention is to provide means to obtain improved lanthanide chelate labels to be used in specific bioaffinity based binding assays, such as immunoassays, DNA hybridization assays, receptor binding assays, immunocytochemical or immunohistochemical assays utilizing fluorometric or time-resolved fluorometric determination of the specific luminescence.

The chelates of this invention have to combine several important features in the single label, such as:

1. high absorptivity at suitable wavelength (preferably over 300 nm), 2. efficient energy transfer from the UV absorbing part (triplet sensitizer) to the chelated lanthanide(III) ion, 3. sufficiently high energy gap (preferable over 2000 $cm^{-1}$) between the triplet state of the donor ligand and the emitting level of the $Tb^{III}$ ion ($^5D_4$ ca. 20500 $cm^{-1}$) to prevent energy back transfer, 4. a strongly chelating part to create a) the thermodynamic stability required for storing the labelled reactants for extended periods of time, and b) high kinetic stability to allow the use of reactants in conditions where competing metal ions or chelating agents may be present, 5. a chelating part forming as complete protection of the chelated ion as possible, preferably nine-dentate ligand, 6. a functional group allowing efficient coupling of the chelate to be used as a binding reactant (e.g., antibody) without destroying its binding properties and decreasing the luminescence properties of the label.

In addition, the chelate has to be highly hydrophilic and possess low nonspecific binding affinity to proteins or surfaces used in the analysis.

In one aspect, therefore, the present invention provides a detectable molecule comprising a biospecific binding reactant attached to a luminescent lanthanide chelate comprising a lanthanide ion and a chelating ligand of the formula

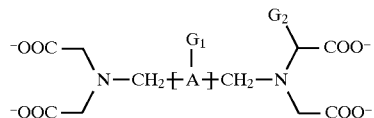

wherein
a) —A— is a bivalent aromatic structure selected from the group consisting of

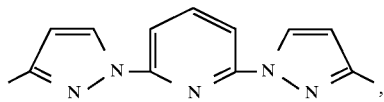

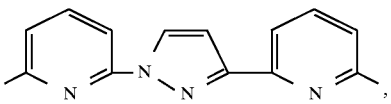

and

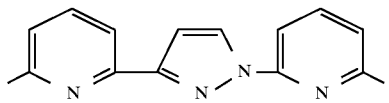

b) one of the groups $G_1$ or $G_2$ is selected from a group consisting of hydrogen, chloro, bromo, iodo, cyano, phenyl, alkyl and alkoxy, with the proviso that said alkyl contains 1–6 carbon atoms; and the other group $G_1$ or $G_2$ is a bridge which does not participate in the chelating process and which is formed of one to four moieties, each moiety being selected from the group consisting of phenylene, alkylene containing 1–8 carbon atoms, ethynediyl (—C≡C—), ether (—O—), thioether (—S—) and amide (—CO—NH— and —NH—CO—);

c) one of the two groups $G_1$ or $G_2$ is used for coupling to a biospecific binding reactant via thiourea (—NH—CS—NH—), aminoacetamide (—NH—CO—CH$_2$—NH—), amide (—NH—CO— and —CO—NH—), aliphatic thioether (—S—), disulfide (—S—S—) or 6-substituted-1,3,5-triazine-2,4-diamine; and d) the lanthanide ion is europium(III), terbium(III), dysprosium (III) or samarium (III).

In another aspect, this invention relates to the use of a detectable molecule as defined above in biospecific binding assays.

The biospecific binding reactant is selected from a group consisting of an antibody, an antigen, a receptor ligand, a specific binding protein, and a DNA- or RNA-probe.

In yet another aspect, this invention provides a luminescent lanthanide chelate comprising a lanthanide ion and a chelating ligand of the formula

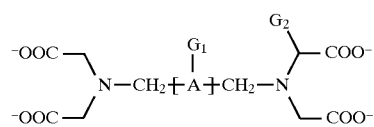

wherein
a) —A— is a bivalent aromatic structure selected from the group consisting of

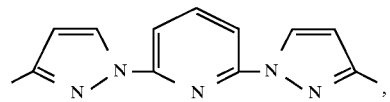

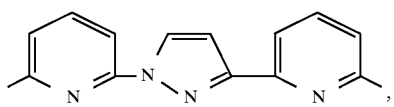

and

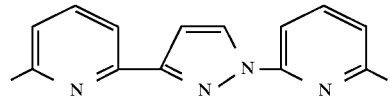

b) one of the groups $G_1$ or $G_2$ is selected from a group consisting of hydrogen, chloro, bromo, iodo, cyano, phenyl, alkyl and alkoxy, with the proviso that said alkyl contains 1–6 carbon atoms; and the other group $G_1$ or $G_2$ is a substituent which in the chelating process and which is formed of one to four moieties, each moiety being selected from the group consisting of phenylene, alkylene containing 1–8 carbon atoms, ethynediyl (—C≡C—), ether (—O—), thioether (—S—) and amide (—CO—NH— and —NH—CO—), and additionally contains one moiety selected from a group containing hydroxy, nitro, amino, aminooxy, carboxyl, aldehyde or mercapto groups or an activated form made from them such as isocyanato, isothiocyanato, diazonium, bromoacetamideo, iodoacetamido, reactive esters, pyridyl-2-dithio or 6-substituted 4-chloro-1,3,5-triazin-2-ylamino;

c) one of the two groups $G_1$ or $G_2$ is used for coupling to a biospecific binding reactant; and d) the lanthanide ion is europium(III), terbium(III), dysprosium (III) or samarium (III).

The substituents in 6-substituted-1,3,5-triazine-2,4-diamine and 6-substituted 4-chloro-1,3,5-triazin-2-ylamino can be selected from the group consisting of hydrogen, halogen, alkoxy, aryloxy, amino, lower alkyl, substituted amino or thioesters, and preferably one selected from chloro, fluoro, ethoxy, 2-methoxyethoxy, 2-cyanoethoxy, 2,2,2-trifluoroethoxy, thiophenoxy or ethoxycarbonylthiomethoxy.

The term "luminescent" shall in this invention be understood to mean "photoluminescent" as already stated above.

The term "bivalent" shall be understood to mean a chemical group with two exactly known binding sites for two covalent bonds to two neighboring atoms.

According to a preferable embodiment of the invention the lanthanide ion is either europium (III) or terbium (III).

The invention is exemplified also with the following examples describing the dependence of the luminescence intensity on the triplet state of ligands and demonstrating the importance of the triplet state of the labels on the luminescence intensity also after coupling the labels to biospecific binding molecules (e.g., antibody). Also an example of chelate coupling to a protein and a standard curve of labelled antibody are given.

The structures and the synthetic routes employed in the experimental part are shown in reaction schemes 1 to 11. Scheme 1 illustrates the synthesis of compounds 1 to 4 exemplified by Examples 1 to 4. Scheme 2 illustrates the synthesis of compounds 5, 7 and 8 exemplified by Examples 5 to 7. Scheme 3 illustrates the synthesis of compound 9 exemplified by Example 8. Scheme 4 illustrates the synthesis of compounds 10 to 19 exemplified by Examples 9 to 18. Scheme 5 illustrates the synthesis of compounds 20 to 27 starting from one of the compounds 18 or 19 as described in Examples 19–26. Scheme 6 illustrates the synthesis of compounds 28 to 31 starting from one of the compounds 22 or 23 and 4 according to Examples 17–30. Scheme 7 illustrates the synthesis of chelates 32 to 36 starting from one of the compounds 30 or 31 as described in Examples 31–35. Scheme 8 illustrates the synthesis of compounds 39 and 40 exemplified by Examples 36 and 37. Scheme 9 illustrates the synthesis of chelates 41–43 starting from compound 40 as described in Examples 38–40. Scheme 10 illustrates the synthesis of compounds 15, 25 and 44–46 starting from compound 13 as described in Examples 41–45. Scheme 11 illustrates the synthesis of chelates 47–49 starting from compound 46 according to Examples 46–48.

EXAMPLE 1

The synthesis of copper(II) complex of bis[2-amino-6-(4-nitrobenzamido)hexanoic acid)](1).

An aq. soln. (170 ml) of $CuSO_4 \times 5H_2O$ (12.5 g, 50 mmol) was added to a soln. of L-lysine×HCl (18.3 g, 100 mmol), NaOH (4.0 g, 100 mmol) and $H_2O$ (170 ml). After stirring for 0.5 h at r.t., NaOH (4.0 g, 100 mmol) was added, and the reaction mixture was cooled in an ice bath. A soln. of 4-nitrobenzoylchloride (37.1 g, 200 mmol) and 1,4-dioxane (250 ml) was added within 5 min, and the mixture was maintained basic with 1M NaOH. After stirring for 0.5 h in an ice bath, the basic mixture was stirred for 14 h at r.t., filtered, washed with cold $H_2O$ and EtOH. Yield: 31.2 g (96%). IR (KBr): 3412, 3279, 3151 (N—H), 1640, 1620, 1605 (C=O), 1528 ($NO_2$), 1349 ($NO_2$).

EXAMPLE 2

The synthesis of the sodium salt of 2-amino-6-(4-nitrobenzamido)hexanoic acid) (2).

A mixture of compound 1 (31.2 g, 47.8 mmol), disodium salt of (ethylenedinitrilo)tetra(acetic acid)×$2H_2O$ (21.9 g, 58.8 mmol) and $H_2O$ (410 ml) was stirred for 3 h at 80°. The cold mixture was filtered, washed with cold $H_2O$ and EtOH. Yield: 19.1 g (63%). IR (KBr): 3422, 3334 (N-H), 1639, 1603 (C=O), 1522, 1352 ($NO_2$). $^1$H-NMR ($D_2O$, ($D_6$) DMSO): 1.33–1.47 (m, 2H); 1.55–1.64 (m, 2H); 1.68–1.87 (m, 2H); 3.33 (t, J=7.0, 2H); 3.42 (t, J=5.8, 1H); 8.01 (d, J=8.8, 2H); 8.34 (d,J=8.8, 2H).

EXAMPLE 3

The synthesis of methyl 2-amino-6-(4-nitrobenzamido) hexanoate (3).

$SOCl_2$ (12.4 ml, 0.17 mmol) was dropped slowly into cooled MeOH (250 ml). After stirring for 0.5 h at r.t., compound 2 (13.5 g, 42.5 mmol; twice co-evaporated with toluene (200 ml)) was added and the mixture refluxed for 3 h. After evaporation, the residue was dissolved into $CHCl_3$ (150 ml), neutralized with sat. $NaHCO_3$ and dried ($Na_2SO_4$).

The product was purified by FC (silica gel, first $CHCl_3$, then 5% MeOH): 8.54 g (65%). IR (film): 3380, 3299 N—H), 1732, 1650 (C=O), 1524, 1347 ($NO_2$), 1200 (C—O). $^1$H-NMR ($CDCl_3$): 1.46–1.57 (m, 2H); 1.58–1.89 (m, 4H); 3.46–3.53 (m, 3H); 3.73 (s, 3H); 6.64 (t, J=5.4, 1H); 7.95 (d, J=8.5, 2H); 8.24 (d, J=8.5, 2H).

EXAMPLE 4

The synthesis of methyl 2-[N-(methoxycarbonylmethyl) amino]-6-(4-nitrobenzamido)hexanoate (4).

A mixture of compound 3 (4.27 g, 13.8 mmol), methyl bromoactate (1.31 ml, 13.8 mmol), dry $K_2CO_3$ (9.53 g, 69.0 mmol) and dry MeCN (80 ml) was refluxed for 4 h, filtered and evaporated. The product was purified by FC (silica gel, petroleum ether (40°–60°)/EtOAc 2:5, then 0:1): 4.52 (86%). IR (film): 3333 (N—H), 1738, 1651 (C=O), 1526, 1348 ($NO_2$), 1207 (C—O). $^1$H-NMR ($CDCl_3$): 1.42–1.60 (m, 2H); 1.60–1.81 (m, 4H); 2.18 (bs, 1H); 3.31 (dd, J=5.6, 7.1, 1H); 3.35 (d, J=17.4, 1H); 3.44–3.50 (m, 2H); 3.47 (d, J=17.4); 3.71 (s, 3H); 3.73 (s, 3H); 7.00 (t, J=5.4, 1H); 7.99 (d, J=8.5, 2H); 8.25 (d, J=8.5, 2H).

EXAMPLE 5

The synthesis of methyl 2-amino-3-(4-nitrophenyl) propionate (5).

This compound (5) was synthesized from 4-nitro-L-phenylalanine×$H_2O$ using a method analogous to the synthesis described in Example 3. Yield: 82%. IR (KBr): 3384, 3314 (N—H), 1737 (C=O), 1518, 1347 ($NO_2$), 1200 (C—O). $^1$H-NMR ($CDCl_3$): 2.98 (dd, J=7.8, 13.7, 1H); 3.18 (dd, J=5.4, 13.7, 1H); 3.69–3.81 (m, 1H); 3.73 (s, 3H); 7.40 (d, J=8.8, 2H); 8.17 (d, J=8.8, 2H).

EXAMPLE 6

The synthesis of methyl 2-[N-(methoxycarbonylmethyl) amino]-3-(4-nitrophenyl)propionate (7).

This compound (7) was synthesized from compound 5 using a method analogous to the synthesis described in Example 4. FC (silica gel, first $CH_2Cl_2$, then 5% MeOH/ $CH_2Cl_2$). Yield: 36%. IR (KBr): 3342 (N—H), 1740 (C=O), 1519,1347 ($NO_2$), 1203 (C—O). $^1$N-NMR ($CDCl_3$): 3.04 (dd, J=7.3, 13.7, 1H); 3.13 (dd, J=6.3, 13.7, 1H); 3.36 (d, J=17.3, 1H); 3.42 (d, J=17.3, 1H); 3.63 (dd, J=6.3, 7.3, 1H); 3.69 (s, 3H); 3.70 (s, 3H); 7.39 (d, J=8.8, 2H); 8.16 (d, J=8.8, 2H).

EXAMPLE 7

The synthesis of methyl 2-[N-(methoxycarbonylmethyl) amino]-6-[N-(benzyloxycarbonyl)amino]hexanoate (8).

This compound (8) was synthesized from 6 using a method analogous to the synthesis described in Example 4. FC (silica gel, petroleum ether (40°–60° )/EtOAc first 5:3, then 2:5). Yield: 48%. IR (KBr): 3343 (N—H), 1736 (C=O), 1244 (C—O). $^1$N-NMR ($CDCl_3$): 1.35–1.90 (m, 6H); 3.19 (q, J=6.3, 2H); 3.28 (t, J=6.5, 1H); 3.34 (d,J=17.6, 1H); 3.44 (d, J=17.6, 1H); 3.71 (s, 3H); 3.72 (s, 3H); 5.09 (s, 2H); 7.28–7.40 (m, 5H).

EXAMPLE 8

The synthesis of methyl N-(2-oxo-tetrahydrofur-3-yl) aminoacetate (9).

This compound (9) was synthesized from (±)-α-amino-γ-butyrolactone×HBr using a method analogous to the synthesis described in Example 4. FC (silica gel, $CHCl_3$). Yield: 31%. IR (KBr): 3333 (N—H), 1770, 1740 (C=O), 1216, 1165 (C—O). $^1$H-NMR (CDCl$_3$): 2.05–2.18 (m, 1H); 2.47–2.57 (m, 1H); 3.57 (d, J=17.6, 1H); 3.63 (d, J=17.6, 1H); 3.64 (dd, J=8.1, 9.8, 1H); 3.75 (s, 3H); 4.21 (dt, J=6.3, 9.8, 1H); 4.42 (dt, J=2.3, 8.8, 1H).

EXAMPLE 9

The synthesis of 3-(N,N-dimethylamino)-1-(2-pyridyl)-2-propen-1-one (10).

A mixture of N,N-dimethylformamide dimethyl acetal (6.65 g, 55.8 mmol) and 2-acetylpyridine (5.63 g, 46.5 mmol) was heated at 100° C. for 4 hours. After evaporation, petroleum ether (40°–60°, 50 ml) was added, the solid material was filtered, and washed with petroleum ether (40°–60°). Yield: 6.76 g (83%). UV (EtOH): 357, 245. IR (film): 1637 (C═O). $^1$H-NMR (CDCl$_3$): 3.00 (s, 3H); 3.18 (s, 3H); 6.45 (bd, J=12.6, 1H); 7.36 (ddd, J=1.2, 4.0, 7.0, 1H); 7.80 (dt, J=1.7, 7.8, 1H); 7.91 (d, J=12.6, 1H); 8.15 (bd, J=7.8, 1H); 8.63 (ddd, J=1.0, 1.7, 4.9, 1H).

EXAMPLE 10

The synthesis of 3-(2-pyridyl)pyrazole (11).

A mixture of compound 10 (6.66 g, 37.8 mmol), NH$_2$NH$_2$×H$_2$O (7.57 g, 151 mmol) and EtOH was stirred for 2 h at r.t., and was evaporated. Yield: 5.33 g (97%). UV (EtOH): 281, 248. IR (film): 3156 (N—H), 1594 (arom). $^1$H)NMR (CDCl$_3$): 6.81 (d,J=1.9, 1H); 7.23–7.26 (m, 1H); 7.67 (d, J=1.9, 1H); 7.74–7.76 (m, 2H); 8.67 (dd, J=1.2, 4.9, 1H).

EXAMPLE 11

The synthesis of 1,3-di(2-pyridyl)pyrazole hydrobromide (12).

A mixture of compound 11 (3.29 g, 22.7 mmol) and 2-bromopyridine (6.37 g, 40.3 mmol) was heated for 20 h at 185° C. The mixture was triturated with acetone (50 ml) and filtered. The product was purified with FC (silica gel, CHCl$_3$): 6.10 g (89%). UV (EtOH): 296, 220 (sh). IR (KBr): $^1$H-NMR (CDCl$_3$): 17.32 (ddd, J=0.9, 4.9, 7.3, 1H); 7.88 (ddd, J=1.5, 6.1, 7.3, 1H); 7.94 (dt, J=1.8, 8.1, 1H); 7.97 (d, J=2.8, 1H); 8.30 (d, J=8.1, 1H); 8.46–8.50 (m, 2H); 8.54 (bd,J=8.1, 1H); 8.73 (d, J=2.8, 1H); 9.00 (bd, J=4.9, 1H). $^{13}$C-NMR (CDCl$_3$): 106.6, 112.6, 120.4, 121.5, 122.9, 128.4, 136.6, 138.6, 148.0, 149.5, 151.5, 151.8, 153.9.

EXAMPLE 12

The synthesis of 1,3-di(2-pyridyl)pyrazole (13).

A mixture of compound 11 (22.2 g, 153 mmol) and 2-bromopyridine (42.3 g, 268 mmol) was heated for 20 h at 190° C. The cooled mixture was dissolved in hot H$_2$O (200 ml) and the pH was adjusted to basic with solid Na$_2$CO$_3$. After cooling, the precipitate was filtered and washed with cold H$_2$O. Yield: 32.9 g (97%). UV (EtOH): 294, 283, 224. IR (KBr): 1593, 1578 (arom). $^1$H-NMR (CDCl$_3$): 7.14 (d, J=2.6, 1H); 7.21 (ddd, J=1.0, 4.9, 7.3, 1H); 7.27 (ddd, J=1.1, 4.9, 7.3, 1H); 7.79 (dt, J=1.7, 7.3, 1H); 7.85 (dt, J=1.7, 7.3, 1H); 8.12–8.16 (m, 2H); 8.44 (dd, J=1.7, 4.9, 1H); 8.64 (d, J=2.6, 1H); 8.68 (bd, J=4.9, 1H).

EXAMPLE 13

The synthesis of 1,3-di(2-pyridyl)pyrazole N,N"-dioxide (14).

3-chloroperbenzoic acid (251 g, 50–55%, ~730 mmol) was added in 7 portions to a solution of compound 13 (10.0 g, 45.0 mmol) in CH$_2$Cl$_2$ (1700 ml), and the mixture was stirred for 18 days at r.t.. H$_2$O (1400 ml) was added and the pH was adjusted to 10 with solid Na$_2$CO$_3$. The phases were separated and the water phase was extracted with CHCl$_3$/EtOH (3:1, 5×400 ml, 6×200 ml). The combined organic phase was dried with Na$_2$SO$_4$ and evaporated to dryness. The product was purified with FC (silica gel, MeOH/CHCl$_3$ 1:9): 7.25 g (63%). UV (EtOH): 307, 278, 257, 220. IR (film): 1228 (N—O). $^1$H-NMR (CDCl$_3$): 7.23–7.27 (m, 1H); 7.27–7.31 (m, 1H); 7.36–7.41 (m, 1H); 7.44–7.48 (m, 1H); 7.84 (d, J=2.7, 1H); 8.20 (dd, J=2.0, 8.3, 1H); 8.29 (dd, J=2.0, 8.1, 1H); 8.39–8.43 (m, 2H); 9.42 (d, J=2.7, 1H). $^{13}$C-NMR (CDCl$_3$): 110.7, 120.3, 122.6, 124.9, 125.6, 126.2, 127.3, 128.0, 129.6, 130.0, 133.8, 140.8, 141.0.

EXAMPLE 14

The synthesis of 4-bromo-1,3-di(2-pyridyl)pyrazole N,N"-dioxide (15).

This compound (15) was synthesized from compound 12 using a method analogous to the synthesis described in Example 13. Yield: 30%. UV (EtOH): 295 (sh), 278, 259, 240 (sh). IR (film): 1256 (n→O). $^1$H-NMR (CDCl$_3$): 7.23–7.27 (m, 1H); 7.32–7.43 (m, 3H); 7.52–7.55 (m, 1H); 8.08–8.10 (m, 1H); 8.34–8.36 (m, 1H); 8.39–8.40 (m, 1H); 9.48 (s, 1H).

EXAMPLE 15

The synthesis of 1,3-bis(6-cyano-2-pyridyl)pyrazole (16).

A mixture of compound 14 (7.20 g, 28.3 mmol), CH$_2$Cl$_2$ (250 ml) and Me$_3$SiCN (28.08 g, 283 mmol) was stirred at r.t. for 15 min. Benzoyl chloride (15.88 g, 113 mmol) was added and stirring was continued overnight. After evaporation to half a volume, 10% K$_2$CO$_3$ (350 ml) was added, the mixture was stirred for 2 h and filtered. Yield: 5.59 g (73%). UV (EtOH): 279 (sh), 275. IR (KBr): 2238 (C≡N), 1592, 1575 (arom). $^1$H-NMR ((D6)-DMSO): 7.25 (d, J=2.7, 1H); 8.08 (d, J=7.9, 2H); 8.21 (t, J=7.9, 1H); 8.31 (t, J=7.9, 1H); 8.40 (d, J=7.9, 1H); 8.44 (d, J=7.9, 1H); 8.80 (d, J=2.7, 1H).

EXAMPLE 16

The synthesis of 4-bromo-1,3-bis(6-cyano-2-pyridyl) pyrazole (17).

This compound (17) was synthesized from compound 15 using a method analogous to the synthesis described in Example 15. Yield: 56%. IR (KBr): 2237 (C≡N), 1590, 1574 (arom). $^1$H-NMR (CDCl$_3$): 7.67 (d, J=8.0, 1H); 7.74 (d, J=8.0, 1H); 7.96 (t, J=8.0, 1H); 8.03 (t, J≦8.0, 1H); 8.29 (d, J=8.0, 1H); 8.34 (d, J=8.0, 1H); 8.74 (s, 1H).

EXAMPLE 17

The synthesis of dimethyl 1,3-di(2-pyridyl)pyrazole-6,6'-dicaboxylate (18).

A mixture of compound 16 (1.99 g, 7.3 mmol), sat. CH$_3$COOH (31 ml) and conc. H$_2$SO$_4$ (31 ml) was refluxed for 2 h, poured into ice H$_2$O (400 ml), filtered, treated with acetone, and the precipitate removed by centrifugation. SOCl$_2$ (1.8 ml, 24.3 mmol) was dropped slowly to cooled MeOH (130 ml). After stirring for 15 min at r.t., the above precipitate was added, and the mixture was refluxed for 4.5 h. After evaporation to a half volume, CHCl$_3$ (100 ml) was added, the mixture was neutralized with sat. NaHCO$_3$. The aq. phase was extracted with CHCl$_3$ (2×50 ml), the org. phase dried with Na$_2$SO$_4$, and evaporated. Yield: 1.77 g (66%). UV (EtOH): 293, 220 (sh). IR (KBr): 1741 (C═O), 1588 (arom), 1234, 1141 (C—O). $^1$H-NMR (CDCl$_3$): 4.03 (s, 3H); 4.04 (s, 3H); 7.28 (d, J=2.7, 1H); 7.94 (t, J=7.8, 1H); 8.00 (t, J=7.6, 1H); 8.04 (dd, J=1.5, 7.6, 1H); 8.11 (dd, J=1.0, 7.8, 1H); 8.32 (dd, J=1.0, 7.8, 1H); 8.34 (dd, J=1.5, 7.6, 1H); 8.79 (d, J=2.7, 1H).

EXAMPLE 18

The synthesis of dimethyl 4-bromo-1,3-di(2-pyridyl) pyrazole-6,6'-dicarboxylate (19).

This compound (19) was synthesized from compound 17 using a method analogous to the synthesis described in Example 17. Yield: 57%. UV (EtOH): 299. IR (film): 1739 (C=O), 1588 (arom), 1250, 1141 (C—O). $^1$H-NMR (CDCl$_3$): 4.04 (s, 3H); 4.05 (s, 3H); 7.98 (t, J=7.9, 1H); 8.01 (t, J≦7.9, 1H); 8.07 (d, J=7.9, 1H); 8.19 (d, J=7.9, 1H); 8.27 (d,J=7.9, 1H); 8.34 (d, J=7.9, 1H); 8.87 (s, 1H).

EXAMPLE 19

The synthesis of 1,3-di(2-pyridyl)pyrazole-6,6'-dimethanol (20).

NaBH$_4$ (0.82 g, 21.6 mmol) was added to a suspension of compound 18 (1.76 g, 5.2 mmol) and abs. EtOH (35 ml). After stirring for 3 h at r.t., the mixture was refluxed for 1 h. The soln. was evaporated, sat. NaHCO$_3$ (40 ml) was added, the mixture brought to boiling. The cold mixture was filtered and washed with cold H$_2$O. Yield: 1.47 g (86%). UV (EtOH): 299, 225(sh). IR (KBr):1600, 1582 (arom). $^1$H-NMR ((D6)-DMSO): 4.62 (s, 2H); 4.64 (s, 2H); 5.50 (bs, 1H); 5.56 (bs, 1H); 7.09 (d, J=2.4, 1H); 7.46 (d, J=7.8, 1H); 7.47 (d, J=7.8, 1H), 7.90 (d, J=7.8, 1H); 7.91 (t, J=7.8, 1H); 7.98 (d, J=7.8, 1H); 8.04 (t, J=7.8, 1H); 8.68 (d, J=2.4, 1H).

EXAMPLE 20

The synthesis of 4-bromo-1,3-di(2-pyridyl)pyrazole-6,6'-dimethanol (21).

This compound (21) was synthesized from compound 19 using a method analogous to the synthesis described in Example 19. UV (EtOH): 301. IR (KBr): 1600, 1575 (arom). $^1$H-NMR (CDCl$_3$): 3.05 (t, J=5.1, 1H); 4.48 (t, J=5.1, 1H); 4.82 (d, J=5.1, 1H); 7.20 (d, J=7.6, 1H); 7.24 (d, J=7.6, 1H); 7.80 (t, J=7.6, 1H); 7.88 (t, J=7.6, 1H); 7.99 (d, J=7.6, 1H); 8.04 (d, J=7.6, 1H); 8.71 (s, 1H).

EXAMPLE 21

The synthesis of 1,3-bis(6-bromomethyl-2-pyridyl)pyrazole (22).

A mixture of dry DMF (20 ml) and PBr$_3$ (0.83 ml, 8.80 mmol) was stirred at r.t. for 15 min. Compound 20 (1.24 g, 4.40 mmol) was added in small portions, and the stirring was continued overnight. After neutralization with saturated NaHCO$_3$ solution, the precipitation was filtered, washed with cold H$_2$O and MeCN. The product was purified by FC (silica gel, CH$_2$Cl$_2$): 0.71 g (40%). UV (EtOH): 302, 225 (sh). IR (KBr): 1598, 1577 (arom). $^1$H-NMR (CDCl$_3$): 4.56 (s, 2H); 4.63 (s, 2H); 7.16 (d, J=2.7, 1H); 7.34 (d, J=7.7, 1H); 7.43 (d, J=7.7, 1H); 7.78 (t, J=7.7, 1H); 7.84 (t, J=7.7, 1H); 8.04 (d, J=7.7, 2H); 8.67 (d, J=2.7, 1H). $^{13}$C-NMR (CDCl$_3$): 33.2, 34.1, 107.0, 111.8, 119.6, 121.0, 122.7, 128.6, 130.3, 137.6, 139.7, 151.5, 153.9, 155.5, 156.6.

EXAMPLE 22

The synthesis of 4-bromo-1,3-bis(6-bromomethyl-2-pyridyl)pyrazole (23).

This compound (23) was synthesized from compound 21 using a method analogous to the synthesis described in Example 21. Yield: 48%, UV (EtOH): 302, 298, 230 (sh). IR (KBr): 1598, 1577 (arom). $^1$H-NMR (CDCl$_3$): 4.54 (s, 2H); 4.68 (s, 2H); 7.37 (dd, J=0.7, 7.6, 1H); 7.52 (dd, J=0.7, 7.6); 7.82 (t, J=7.6, 1H); 7.85 (t, J=7.6, 1H); 7.95 (dd, J=0.7, 7.6, 1H); 8.01 (dd, J=0.7, 7.6, 1H); 8.75 (s, 1H).

EXAMPLE 23

The synthesis of tetra(tert-butyl) 2,2',2'',2'''-{[6,6'-(pyrazole-1'',3''-diyl)bis(pyridine)-2,2'-diyl]bis(methylenenitrilo)}tetrakis(acetate) (24).

A mixture of compound 22 (15 mg, 37 μmol), di(tert-butyl) aminobis(acetate) (18 mg, 74 μmol), dry K$_2$CO$_3$ (50 mg, 370 μmol) and dry MeCN (300 μl) was refluxed 4.5 h. After evaporation, the residue was taken into CHCl$_3$ (10 ml), washed with H$_2$O (2×5 ml) and dried with Na$_2$SO$_4$. Yield: 27 mg (100%). UV (EtOH): 301, 215 (sh). IR (film): 1734 (C=O); 1143 (C—O). $^1$H-NMR (CDCl$_3$): 1.47 (s, 36H); 3.53 (s, 4H); 3.57 (s, 4H); 4.07 (s, 2H); 4.15 (s, 2H); 7.12 (d, J=2.4, 1H); 7.52 (d, J=7.7, 1H); 7.61 (d, J=7.7, 1H); 7.76 (t, J=7.7, 1H); 7.82 (t, J=7.7, 1H); 7.98 (d, J=7.7, 1H); 8.01 (d, J=7.7, 1H); 8.63 (d, J=2.4, 1H).

EXAMPLE 24

The synthesis of tetra(tert-butyl) 2,2',2'',2'''-{[6,6'-(4''-bromopyrazole-1'',3''-diyl)bis(pyridine)-2,2'-diyl]bis(methylenenitrilo)}tetrakis(acetate) (25).

This compound (25) was synthesized from compound 23 using a method analogous to the synthesis described in Example 23. Yield: 79%. UV (EtOH): 300, 225. IR (film): 1732 (C=O), 1144 (C—O). $^1$H-NMR (CDCl$_3$): 1.47 (s, 18H); 1.48 (s, 18H); 3.53 (s, 4H); 3.57 (s, 8H); 4.06 (s, 2H); 4.15 (s, 2H); 7.54 (d, J=7.6, 1H); 7.72 (d, J=8.0, 1H); 7.79 (t, J=7.6, 1H); 7.82 (t, J=8.0, 1H); 7.91 (d, J=7.6, 1H); 7.95 (d, J=8.0, 1H); 8.70 (s, 1H).

EXAMPLE 25

The synthesis of 2,2',2'',2'''-{[6,6'-(pyrazole-1'',3''-diyl)bis(pyridine)-2,2'-diyl]bis(methylenenitrilo)}tetrakis(acetic acid) (26).

A solution of compound 24 (63 mg, 65 μmol) in CF$_3$COOH (1.2 ml) was stirred at r.t. for 2 h. After evaporation to dryness, the residue was triturated with Et$_2$O, filtered and washed with Et$_2$O. UV (H$_2$O): 302, 224. UV ([Eu$^{III}$ (26)], H$_2$O): 330, 320, 287, 279, 250 (sh). IR (KBr) :2734 (C=O), 1204 (C—O). $^1$H-NMR ((D6)-DMSO): 3.62 (s, 4H); 3.67 (s, 4H); 4.10 (s, 2H); 4.16 (s, 2H); 7.13 (d, J=2.2, 1H); 7.52–7.55 (m, 2H); 7.93–7.95 (m, 2H); 8.03–8.05 (m, 2H); 8.68 (d, J=2.2, 1H).

EXAMPLE 26

The synthesis of 2,2',2'',2'''-{[6,6'-(4''-bromopyrazole-1'',3''-diyl)bis(pyridine)-2,2'-diyl]bis(methylenenitrilo)}tetrakis(acetic acid) (27).

This compound (27) was synthesized from compound 25 using a method analogous to the synthesis described in Example 25. UV (H$_2$P): 301, 226. UV ([Eu$^{III}$(27)], H$_2$O): 335 (sh), 323, 287, 280, 250 (sh). IR (KBr): 1734 (C=O), 1202 (C—O). $^1$H-NMR ((D6)-DMSO): 3.67 (s, 4H); 3.73 (s, 4H); 4.15 (s, 2H); 4.18 (s, 2H); 7.56 (d, J=7.6, 1H); 7.63 (d, J=7.6, 1H); 7.91–8.00 (m, 3H); 8.07 (t, J=7.6, 1H); 8.86 (s, 1H).

EXAMPLE 27

The synthesis of tetramethyl 2- and 2''-[4-(4-nitrobenzamido)but-1-yl]-2,2',2'',2'''-{[6,6'-(pyrazole-1'',3''-diyl)bis(pyridine)-2,2'-diyl]bis(methylenenitrilo)}tetrakis(acetate) (28)

Compound 4 (190 mg, 0.5 mmol) was added in two portions within 2 h to a mixture of compound 22 (204 mg, 0.5 mmol), dry K$_2$CO$_3$ (207 mg, 1.5 mmol) and dry MeCN (10 ml). After refluxing for 4 h, dimethyl iminobis(acetate) (81 mg, 0.5 mmol) was added. The mixture was refluxed overnight, filtered, the filtrate evaporated, and the residue was dissolved in dry pyridine (4 ml). After an addition of acetic anhydride (189 mg, 2 mmol), the soln. was stirred for 4 h at r.t., evaporated and the residue co-evaporated twice with toluene. The product was purified by FC (silica gel, petroleum ether (40°–60°)/EtOAc/Et$_3$N 5/1/1): 150 mg (38%). IR (film): 3349, 1732, 1651 (C=O), 1530, 1348 (NO$_2$), 1204 (C—O). $^1$H-NMR (CDCl$_3$): 1.55–1.75 (m, 4+4H); 1.75–1.90 (m, 2+2H); 3.43–3.51 (m, 2+2H); 3.55–3.75 (m, 3+3H); 3.61 (s, 3H); 3.62 (s, 3H); 3.69 (s, 4H); 3.70 (s, 4H); 3.71 (s, 6H); 3.72 (s, 6H); 3.73 (s, 3+3H); 3.95 (d, J=14.6, 1H); 3.99 (d, J=14.6, 1H); 4.05 (d, J=14.6, 1H); 4.08 (s, 2H); 4.09 (d, J=14.6, 1H); 4.13 (s, 2H); 6.83 (bs, 1H); 6.96 (bs, 1H); 6.06 (d, J=2.4, 1H); 7.07 (d, J=2.4, 1H); 7.35 (d, J=7.8, 1H); 7.40 (d, J=7.8, 1H); 7.45 (d, J=7.8, 1H); 7.52 (d, J=7.8, 1H); 7.59 (t, J=7.8, 1H); 7.68 (t, J=7.8, 1H); 7.76 (t, J=7.8, 1H); 7.82 (t, J=7.8, 1H); 7.88–7.98 (m, 2+2H); 7.90 (d, J=8.9. 2H); 7.92 (d, J=8.9, 2H); 8.15 (d, J=8.9, 2H); 8.18 (d, J=8.9, 2H); 8.56 (d, J=2.4, 1H); 8.57 (d, J=2.4, 1H). It was impossible to assign signals to certain isomers. The isomeric ratio according to NMR was 56:44.

EXAMPLE 28

The synthesis of tetramethyl 2- and 2"-[4-(4-nitrobenzamido)but-1-yl]-2,2',2",2'"-{[6,6'-(4"-bromopyrazole-1",3"-diyl)bis(pyridine)-2,2'-diyl]bis(methylenenitrilo)}tetrakis(acetate) (29)

This compound (29) was synthesized from compound 23 using a method analogous to the synthesis described in Example 27. Yield: 30%. IR (film): 3317 (N—H), 1737, 1659 (C=O), 1525, 1347 (NO$_2$), 1210 (C—O). $^1$H-NMR (CDCl$_3$): 1.55–1.70 (m, 4+4H); 1.75–1.88 (m, 2+2H); 3.43–3.50 (m, 2+2H); 3.50–3.75 (m, 3+3H); 3.63 (s, 3H); 3.65 (s, 3H); 3.68 (s, 4H); 3.72 (s, 4+6H); 3.73 (s, 6H); 3.73 (s, 3+3H); 3.95 (d, J=14.6, 1H); 4.05 (d, J=14.6, 1H); 4.08 (s, 2H); 4.09 (d, J=14.6, 1H); 4.13 (d, J=14.6, 1H); 4.17 (s, 2H); 6.82 (bs, 1H); 6.94 (bs, 1H); 7.41 (d,J=7.6, 1H); 7.49 (d, J=7.6, 1H); 7.53 (d, J=7.6, 1H); 7.63 (d, J=7.6, 1H); 7.64 (t, J=7.6, H); 7.70 (t, J=7.6, 1H); 7.80 (t, J=7.6, 1H); 7.83 (t, J=7.6, 1H); 7.88–7.98 (m, 2+2H); 7.93 (d, J=8.8, 2H); 7.96 (d, J=8.8, 2H); 8.17 (d, J=8.8, 2H); 8.20 (d, J=8.8, 2H); 8.65 (s, 1H); 8.66 (s, 1H). It was impossible to assign signals to certain isomers. The isomeric ratio according to NMR was 51:49.

EXAMPLE 29

The synthesis of tetramethyl 2- and 2"-[4-(4-aminobenzamido)but-1-yl]-2,2',2",2'"-{[6,6'-(pyrazole-1",3"-diyl)bis(pyridine)-2,2'-diyl]bis(methylenenitrilo)}tetrakis(acetate) (30)

A mixture of compound 28 (100 mg, 12 mmol), 10% Pd/C (25 mg) and MeOH (20 ml) was stirred under H$_2$ (3.4 atm) for 0.5 h. After filtration, the filtrate was evaporated, and the product purified by FC (silica gel, petroleum ether (40°–60°)/EtOAc 2/5): 58 mg (60%). IR (film): 3348, 3244 (N—H), 1732, 1633 (C=O), 1180 (C—O). $^1$H-NMR (CDCl$_3$): 1.53–1.72 (m, 4+4H); 1.75–1.88 (m, 2+2H); 3.43–3.50 (m, 2+2H); 3.50–3.76 (m, 3+3H); 3.65 (s, 3+3H); 3.69 (s, 4H); 3.70 (s, 4H); 3.72 (s, 6H); 3.73 (s, 6+3H); 3.74 (s, 3H); 4.03 (d, J=14.6, 1+1H); 4.09 (s, 2H); 4.10 (d, J=14.6, 1+1H); 4.20 (s, 2H); 6.60 (d, J=8.5, 2H); 6.61 (d, J=8.5, 2H); 7.08 (d, J=2.4, 1+1H); 7.42 (d, J=7.6, 1H); 7.44 (d, J=7.6, 1H); 7.59 (d, J=8.5, 2H); 7.61 (d, J=8.5, 2H); 7.62 (t, J=7.6, 1H); 7.67 (t, J=7.6, 1H); 7.76 (t, J=7.6, 1H); 7.82 (t, J=7.6, 1H); 7.90 (d, J=7.6, 1H); 7.94 (d, J=7.6, 1H); 7.97 (d, J=7.6, 1H); 7.98 (d, J=7.6, 1H); 8.59 (d, J=2.4, 1+1H). It was impossible to assign signals to certain isomers.

EXAMPLE 30

The synthesis of tetramethyl 2- and 2"-[4-(4-aminobenzamido)but-1-yl]-2,2',2",2'"-{[6,6'-(4"-bromopyrazole-1",3"-diyl)bis(pyridine)-2,2'-diyl]bis(methylenenitrilo)}tetrakis(acetate) (31)

This compound (31) was synthesized from compound 29 using a method analogous to the synthesis described in Example 29. Yield: 65%. IR (film): 3360, 3267 (N—H), 1738, 1627 (C=O), 1209 (C—O). $^1$H-NMR (CDCl$_3$): 1.50–1.70 (m, 4H); 1.75–1.85 (m, 2H); 3.38–3.43 (m, 2H); 3.50–3.76 (m, 3H); 3.57 (s, 3H); 3.69 (s, 4H); 3.72 (s, 3H); 3.75 (s, 6H); 3.97 (d, J=14.6, 1H); 4.08 (d, J=14.6, 1H); 4.09 (s, 2H); 6.63 (d, J=8.5, 2H); 7.47 (d, J=8.0, 1H); 7.50 (d, J=8.0, 1H); 7.58 (d, J=8.5, 2H); 7.70 (t, J=8.0, 1H); 7.85 (t, J=8.0, 1H); 8.01 (d, J=8.0, 1H); 8.04 (d, J=8.0, 1H); 8.65 (s, 1H). Only one isomer was shown.

EXAMPLE 31

The synthesis of 2- and 2"-[4-(4-aminobenzamido)but-1-yl]-2,2',2",2'"-{[6,6'-(pyrazole-1",3"-diyl)bis(pyridine)-2,2'-diyl]bis(methylenenitrilo)}tetrakis(acetato)terbium(III) (32)

A mixture of compound 30 (67 mg, 88 µmol) and 0.5M KOH in EtOH (2.5 ml) was stirred for 1 h at r.t.. Some H$_2$O (0.58 ml) was added and the stirring was continued for 3 h. After evaporation, the residue was dissolved in H$_2$O (1.2 ml) and the pH was adjusted to 6.5 with 5M HCl. An aq. soln. (0.6 ml) of TbCl$_3$ (36 mg, 97 µmol) was added within 15 min and the pH was maintained at 5.0–6.5 with solid NaHCO$_3$. After stirring for 1.5 h at r.t. the pH was adjusted to 8.5 with 1M NaOH. The precipitate was removed by centrifugation, the filtrate triturated with acetone, and the solid material removed by centrifugation and washed with acetone. The solid material was dissolved in H$_2$O (1.0 ml), extracted with phenol, and the phenol phase was treated with H$_2$O (1.0 ml) and Et$_2$O (10 ml). The H$_2$O phase was washed with Et$_2$O (2×10 ml), treated with acetone, and the product removed by centrifugation and washed with acetone. Yield: 30 mg (40%). UV (H$_2$O): 331, 320, 287, 279, 263. IR (KBr): 1617 (C=O), 1388 (C—O).

EXAMPLE 32

The synthesis of 2- and 2"-[4-(4-aminobenzamido)but-1-yl]-2,2',2",2'"-{[6,6'-(4"-bromopyrazole-1",3"-diyl)bis(pyridine)-2,2'-diyl]bis(methylenenitrilo)}tetrakis(acetato)terbium(III) (33)

This compound (33) was synthesized from compound 31 using a method analogous to the synthesis described in Example 31. UV (H$_2$O): 328, 317, 285, 277, 267. IR (KBr): 1602 (C=O), 1407 (C—O).

EXAMPLE 33

The synthesis of 2- and 2"-[4-(4-isothiocyanatobenzamido)but-1-yl]-2,2',2",2'"-{[6,6'-pyrazole-1",3"-diyl)bis(pyridine)-2,2'-diyl]bis(methylenenitrilo)}tetrakis(acetato)terbium(III) (34)

An aq. (0.454 ml) soln. of compound 32 (14 mg, 16 µmol) was added within 15 min to a mixture of thiophosgene (5.0 µl, 64 µmol), NaHCO$_3$ (6.7 mg, 80 µmol) and CHCl$_3$ (0.454 ml). After stirring for 30 min, the aq. phase was washed with CHCl$_3$ (3×1 ml), acetone was added to the aq. soln. and the product removed by centrifugation and washed with acetone. Yield: 13 mg (87%). UV (H$_2$O): 330, 320, 287, 280, 263. IR (KBr): 2099 (S=C'N), 1613 (C=O), 1366 (C—O).

EXAMPLE 34

The synthesis of 2- and 2"-[4-(4-isothiocyanatobenzamido)but-1-yl]-2,2',2",2'"-{[6,6'-(4"-bromopyrazole-1",3"-diyl)bis(pyridine)-2,2'-diyl]bis(methylenenitrilo)}tetrakis(acetato)terbium(III) (35)

This compound (35) was synthesized from compound 33 using a method analogous to the synthesis described in Example 33. Yield: 82%. UV ($H_2O$): 328, 318, 286, 280, 264 (sh). IR (KBr): 2105 (S=C=N), 1603 (C=O), 1404 (C—O).

EXAMPLE 35

The synthesis of 2"- and 2'"-{4-{4-[(4,6-dichloro-1,3,5-triazin-2-yl)amino]benzamido}but-1-yl}-2,2',2",2'"-{[6,6'-(pyrazole-1",3"-diyl)bis(pyridine)-2,2'-diyl]bis(methylenenitrilo)}tetrakis(acetato)terbium(III) (36)

A mixture of 2,4,6-trichloro-1,3,5-triazine (45 mg, 0.25 mmol), acetone (0.25 ml) and $H_2O$ (0.25 ml) was added to a soln. of compound 32 (21 mg, 25 µmol) and 0.1M NaOAC (0.375 ml, pH 4.9). After stirring for 15 min. acetone was added to the mixture, and the precipitate removed by centrifugation and washed with acetone. UV ($H_2O$): 330, 318, 287, 279, 262. IR (KBr): 1609 (C=O), 1388 (C—O).

EXAMPLE 36

The synthesis of trimethyl ethyl 2-[4-(4-nitrobenzamido)but-1-yl]-2,2',2",2'"-{[1,1'-(pyridine-2",6"-diyl)bis(pyrazole)-3,3'-diyl]bis(methylenenitrilo)}tetrakis(acetate) (39)

Compound 37 (EP 298939 B1) (198 mg, 0.5 mmol) (ethyl 2-{[(methoxycarbonyl)methyl]amino}-6-[(4-nitrobenzoyl)amino]hexanate); was added in two portions to a soln. of compound 38 (2,6-bis[3-(bromomethyl)-1H-pyrazol-1-yl]pyridine)s (Remuinán, M. J., Román, H., Alonso, M. T. and Rodríguez-Ubis, J. C., 1993, J. Chem. Soc., Perkin Trans.2, 1099) (200 mg, 0.5 mmol), dry $K_2CO_3$ (207 mg, 1.5 mmol) and dry MeCN (25 ml). After refluxing for 9 h, a soln. of dimethyl iminobis(acetate) (94.5 mg, 0.5 mmol) and dry MeCN (4 ml) was added in two portions. After refluxing for 7 h, the mixture was filtered, the filtrate evaporated and the product purified by FC (silica gel, EtOAc/hexane 3:2): 52%. Anal. calcd for $C_{40}H_{51}N_9O_{11}$: C 57.61; H 6.16; N 15.12. Found: C 57.87; H 6.00; N 14.87.

EXAMPLE 37

The synthesis of trimethyl ethyl 2-[4-(4-aminobenzamido)but-1-yl]-2,2',2",2'"-{[1,1'-(pyridine-2",6"-diyl)bis(pyrazole)-3,3'-diyl]bis(methylenenitrilo)}tetrakis(acetate) (40)

This compound (40) was synthesized from compound 39 using a method analogous to the synthesis described in Example 29. Anal. calcd for $C_{40}H_{53}N_9O_9$: C 59.76; H 6.65; N 15.68. Found: C 60.02; H 6.63; N 15.45.

EXAMPLE 38

The synthesis of 2-[4-(4-aminobenzamido)but-1-yl]-2,2',2",2'"-{[1,1'-(pyridine-2",6"-diyl)bis(pyrazole)-3,3'-diyl]bis(methylenenitrilo)}tetrakis(acetato)terbium(III) (41)

A mixture of compound 40 (270 mg, 0.36 mmol) and 0.5M KOH in EtOH (16 ml) was stirred for 2 h at r.t.. Some $H_2O$ (1.6 ml) was added to the reaction mixture and the stirring was continued for 2 h. After evaporation, the residue was dissolved in $H_2O$ (6 ml) and the pH was adjusted to 6.5 with 5M HCl. An aq. soln. of $TbCl_3$ (134 mg, 0.36 mmol) was slowly added and the pH was maintained at 5.0–6.5 with 2M NaOH. After stirring for 1 h, the precipitate was removed by centrifugation and washed with acetone. Yield: 60%. UV ($H_2O$): 309, 276, 270. IR (KBr): 1616 (C=O), 1400 (C—O). Anal. calcd for $C_{32}H_{33}N_9O_9TbK$: C 43.40; H 3.76; N 14.23. Found: C 42.98; H 4.18; N 13.96.

EXAMPLE 39

The synthesis of 2-[4-(4-isothiocyanatobenzamido)but-1-yl]-2,2',2",2'"-{[1,1'-(pyridine-2",6"-diyl)bis(pyrazole)-3,3'-diyl]bis(methylenenitriol)}tetrakis(acetato)terbium(III) (42)

This compound (42) was synthesized from compound 41 using a method analogous to the synthesis described in Example 33. UV ($H_2O$): 313 (sh), 203, 277, 270 (sh), 253 (sh), 228. IR (KBr): 2077 (S=C=N), 1617 (C=O), 1381 (C—O).

EXAMPLE 40

The synthesis of 2-{4-{4-[(4,6-dichloro-1,3,5-triazin-2-yl)amino]benzamido}but-1-yl}-2,2',2",2'"-{[1,1'-(pyridine-2",6"-diyl)bis(pyrazole)-3,3'-diyl]bis(methylenenitrilo)}tetrakis(acetato)terbium(III) (43)

This compound (43) was synthesized from compound 41 using a method analogous to the synthesis described in Example 35. UV ($H_2O$): 307, 276, 269, 242, 243 (sh). IR (KBr): 1608 (C=O), 1394 (C—O).

EXAMPLE 41

The synthesis of 4-bromo-1,3-di(2-pyridyl)pyrazole (44)

NBS (26.7 g, 150 mmol) and dibenzoylperoxide (1.20 g, 4.95 mmol) was added in 3 portions during 3 d to a boiling soln. of compound 13 (11.1 g, 50.0 mmol) and $CCl_4$ (220 ml). After refluxing an additional 24 h, the cold mixture was filtered and the filtrate washed with sat. $NaHCO_3$ (100 ml), $H_2O$ (100 ml), dried ($Na_2SO_4$) and evaporated. Yield: 14.8 g (98%). IR (KBr): 1598, 1588 (arom). $^1$H-NMR ($CDCl_3$): 7.23–7.26 (m, 1H); 7.32–7.35 (m, 1H); 7.80–7.87 (m, 2H); 8.09 (d, J=7.8, 1H); 8.14 (d, J=8.3, 1H); 8.43 (d, J=4.1, 1H); 8.72 (s, 1H); 8.80 (d, J=3.4, 1H). MS: 300 (100, $M^+$), 302 (98, $[M+2]^+$).

EXAMPLE 42

The synthesis of 4-bromo-1,3-di(2-pyridyl)pyrazole N,N"-dioxide (15).

This compound (15) was synthesized from compound 44 using a method analogous to the synthesis described in Example 13. Yield: 49%.

EXAMPLE 43

The synthesis of tetra(tert-butyl) 2,2',2",2'"-{[6,6'-(4"-bromopyrazole-1",3"-diyl)bis(pyridine)-2,2'-diyl]bis(methylenenitrilo)}tetrakis(acetate) (25)

A suspension of compound 17 (3.79 g, 10.8 mmol) and dry THF (100 ml) was deaerated with $N_2$. $BH_3\cdot$THF (1M, 110 ml) was added within 10 min into the cold reaction mixture. After stirring for 2 h in an ice bath and 3 h at r.t., excess $BH_3$ was destroyed by addition of MeOH, the mixture evaporated and the residue dissolved in MeOH saturated with dry HCl (200 ml). After stirring for 1 h, the mixture was evaporated, and the residue treated with THF (150 ml). The cooled mixture was filtered and the solid material washed with THF. A mixture of this material, $BrCH_2COOC(CH_3)_3$ (2.91 ml, 18.0 mmol), dry (i-$Pr)_2EtN$ (12.0 ml, 67.5 mmol) and dry MeCN (90 ml) was refluxed for 24 h. After evaporation, the residue was dissolved in $CHCl_3$ (100 ml), washed with $H_2O$ (3×50 ml) and dried ($Na_2SO_4$). The product was purified by FC (silica gel, petroleum ether (40°–60°)/AcOEt/$Et_3N$ 10:1:1): 0.97 g (26%).

EXAMPLE 44

The synthesis of tetra(tert-butyl) 2,2',2",2'"-{{6,6'-{4"-[(4-aminophenyl)ethynyl]pyrazole-1",3"-diyl}bis(pyridine)-2,2'-diyl}bis(methylenenitrilo)}tetrakis(acetate) (45).

A mixture of compound 26 (0.49 g, 0.59 mmol), 4-aminophenylacetylene (83 mg, 0.71 mmol; Takalo, H, Kankare, J. and Hänninen, E., 1988, Acta Chem. Scand. B 42, 448), dry Et₃N (3 ml) and dry THF (3 ml) was deaerated with N₂. Bis(triphenylphosphine)palladium(II) chloride (8.5 mg, 12 μmol) and CuI (4.6 mg, 24 μmol) was added and the mixture was stirred for 40 h at 55°–60°. After evaporation, the residue was dissolved in CHCl₃ (20 ml), washed with H₂O (3×10 ml) and dried (Na₂SO₄). The product was purified by FC (silica gel, petroleum ether (40°–60°)/AcOEt first 5:3 then 2:5): 0.12 g (24%). IR (film): 3466, 3372 (N—H), 2215 (C≡C), 1737 (C=O), 1146 (C—O). ¹H NMR (CDCl₃): 1.45 (s, 18H); 1.48 (s, 18H); 3.54 (s, 4H); 3.55 (s, 4H); 4.06 (s, 2H); 4.21 (s, 2H); 6.66 (d, J=8.4, 2H); 7.35 (d, J=8.4, 2H); 7.53 (d, J=7.3, 1H); 7.76 (d, J=7.3, 1H); 7.80 (t, J=7.3, 1H); 7.82 (t, J=7.3, 1H); 8.03 (d, J=7.3, 1H); 8.18 (d, J=7.3, 1H); 8.83 (s, 1H).

EXAMPLE 45

The synthesis of tetra(tert-butyl) 2,2',2",2'''-{{6,6'-{4"-[2-(4-aminophenyl)ethyl]pyrazole-1",3"-diyl}bis(pyridine)-2,2'-diyl}bis(methylenenitrilo)}tetrakis(acetate) (46).

A mixture of compound 45 (115 mg, 0.135 mmol), 10% Pd/C (20 mg) and MeOH (20 ml) was stirred under N₂ (0.69 MPa) for 2.5 h. After filtration, the filtrate was evaporated and the residue was purified by FC (silica gel, petroleum ether (40°–60°)/AcOEt 5:3): 87 mg (75%). IR (film): 3444, 3372 (N—H), 1733 (C=O), 1145 (C—O). ¹H NMR (CDCl₃): 1.44 (s, 18H); 1.47 (s, 18H); 2.84–2.89 (m, 2H); 3.19–3.23 (m, 2H); 3.52 (s, 4H); 3.53 (s, 4H); 4.05 (s, 2H); 4.11 (s, 2H); 6.63 (d, J=7.9, 2H); 7.03 (d, J=7.9, 2H); 7.48 (d, J=7.9, 1H); 7.62 (d, J=7.9, 1H); 7.74 (t, J=7.9, 1H); 7.78 (t, J=7.9, 1H); 7.92 (d, J=7.9, 1H); 7.93 (d, J=7.9, 1H); 8.38 (s, 1H).

EXAMPLE 46

The synthesis of 2,2',2",2'''-{{6,6'-{4"-[2-(4-aminophenyl)ethyl]pyrazole-1",3"-diyl}bis(pyridine)-2,2'-diyl}bis(methylenenitrilo)}tetrakis(acetato)terbium(III) (47).

First, the ester group hydrolysis of compound 45 using a method analogous to the synthesis described in Example 25 gave 2,2',2",2'''-{{6,6'-{4"-[2-(4-aminophenyl)ethyl]pyrazole-1",3"-diyl}bis(pyridine)-2,2'-diyl}bis(methylenenitrilo)}tetrakis(acetic acid). UV (H₂O): 335 (sh), 304, 226 (sh). UV([Eu$^{III}$ (46)], H₂): 325, 289, 279 (sh), 238 (sh). IR (KBr): 1734, 1676, 1636 (C=O), 1376, 1202 (C—O). ¹H NMR ((D₆)-DMSO): 2.96 (t, J=7.7, 2H); 3.22 (t, J=7.7, 2H); 3.59 (s, 4H); 3.60 (s, 4H); 4.07 (s, 2H); 4.11 (s, 2H); 7.15 (d, J=7.7, 2H); 7.33 (d, J=7.7, 2H); 7.50 (d, J=7.7, 1H); 7.57 (d, J=7.7, 1H); 7.89 (d, J≦7.7, 1H); 7.92 (t, J=7.7, 1H); 7.97 (d, J=7.7, 1H); 8.01 (t, J=7.7, 1H); 8.48 (s, 1H). This tetraacid (43 mg, 40 μmol) was dissolved in H₂O (0.75 ml) and the pH was adjusted to 6.5 with solid NaHCO₃. An aq. soln. (0.25 ml) of TbCl₃ (16 mg, 44 μmol) was added within 15 min and the pH was maintained at 5–7. After stirring for 2 h, the pH was raised to 8.5–9.0 with 1M NaOH, the precipitate removed by centrifucation, the filtrate treated with acetone, and the precipitate removed by centrifugation and washed with acetone. Yield: 27 mg (84%). UV (H₂O): 338 (sh), 327, 290, 283 (sh), 239. IR (KBr): 1608 (C=O), 1396 (C—O).

EXAMPLE 47

The synthesis of 2,2',2",2'''-{{6,6'-{4"-[2-(4-isothiocyanatophenyl)ethyl]pyrazole-1",3"-diyl}bis(pyridine)-2,2'-diyl}bis(methylenenitrilo)}tetrakis(acetato)terbium(III) (48).

This compound (48) was synthesized from compound 47 using a method analogous to the synthesis described in Example 33. UV (H₂O): 337 (sh), 326, 289 (sh), 281, 270, 254. IR (KBr): 2115 (S=C=N), 1609 (C=O), 1397 (C—O).

EXAMPLE 48

The synthesis of 2,2',2",2'''-{{6,6'-{4"-{2-[(4,6-Dichloro-1,3,5-triazin-2-yl)amino]ethyl}pyrazole-1",3"-diyl}bis(pyridine)-2,2'-diyl}bis(methylenenitrilo)}tetrakis(acetato)terbium(III) (49).

This compound (49) was synthesized from 47 using a method analogous to the synthesis described in Example 35. UV (H₂O): 321, 290, 251. IR (KBr): 1608 (C=O), 1390 (C—O).

EXAMPLE 49

The luminescence measurements of compound 26 and 27 with Eu$^{III}$ and Tb$^{III}$.

The luminescence parameters for the Eu$^{III}$ and Tb$^{III}$ chelates were measured in borate buffer, pH 8.5. The ligand concentrations were kept at 10 μM, and the lanthanide-ion concentrations varied between 0.1 and 1 μM depending on the luminescence intensities. The measurements were standardized using 0.1 μM Eu$^{III}$ in Wallac Delfia enhancement soln. (molar absortivity 37600, quantum yield 70% and luminescence yield 26320). The emission intensities of the lanthanide chelates were measured using the most intense emission line, at ca. 545 nm for Tb$^{III}$ and 613 for Eu$^{III}$. The Tb$^{III}$ luminescence was corrected for photomultiplier quantum-yield difference (1.39-fold at 545 nm as compared to the value at 613 nm). The phosphorescence spectra were measured in 5:4 mixtures of glycerol (purified) and water (quartz dist.) buffered by tris(hydroxymethyl)aminomethane and HCl (TRIS-HCl buffer). Concentration of Gd$^{III}$ (added as perchlorate) was 10 μM and ligand 30 μM.

TABLE 1

The triplet state energy levels (E) of Gd$^{III}$ chelates of compounds 26, 27, and TERPY, and the excitation maxima ($\lambda_{exc}$), luminescence decay times (τ) and luminescence yields (ε · Φ) of the Eu$^{III}$ chelates of compounds 26, 27 and TERPY.

| Compound | $\lambda_{exc}$[nm] | τ[μs] | ε · Φ | E[cm⁻¹] |
|---|---|---|---|---|
| Eu$^{III}$(26) | 327 | 1000 | 1550 | 23000 |
| Eu$^{III}$(27) | 329 | 1020 | 1630 | 23100 |
| Eu$^{III}$(TERPY) | 334 | 1310 | 2100 | 22400 |

TABLE 2

The triplet state energy levels (E) of Gd$^{III}$ chelates of compounds 26, 27, and TERPY, and the excitation maxima ($\lambda_{exc}$), luminescence decay times (τ) and luminescence yields (ε · Φ) of the Tb$^{III}$ chelates of compounds 26, 27 and TERPY.

| Compound | $\lambda_{exc}$[nm] | τ[μs] | ε · Φ | E[cm⁻¹] |
|---|---|---|---|---|
| Tb$^{III}$(26) | 327 | 2810 | 8810 | 23000 |
| Tb$^{III}$(27) | 331 | 2550 | 8900 | 23100 |
| Tb$^{III}$(TERPY) | 333 | 1100 | 3800 | 22400 |

EXAMPLE 50

Coupling of the chelates to Protein.

The activated chelates were coupled to a model protein (PSA-antibody, clone H50) by incubating the chelate with IgG (1 mg/ml) in carbonate buffer (500 μl, pH 9.8) overnight using a 30-fold molar reactant-to-protein ratio. After the coupling reaction, the protein was purified on a column of Superdex 200 prep grade by eluting with 50 mM Tris-HCl buffer (pH 7.75) containing 0.15M NaCl and 0.05% NaN$_3$ soln. The fractions corresponding to labelled monomeric IgG were collected. The chelate concentrations in the protein fractions were measured from both the absorptions of the conjugated chelate at 330 nm and the total Tb$^{III}$ ion concentration measured by the dissociative fluorescence enhancement system. The purified protein conjugate and the labelling ratio (chelates power protein) were quantitated by calculating the protein yield or by measuring the absorbance at 280 nm and subtracting the absorption caused by the added chelate.

TABLE 3

The excitation maxima ($\lambda_{exc}$), luminescence decay times ($\tau$) and luminescence yields ($\epsilon \cdot \Phi$) of the Tb$^{III}$ chelates 34, 42, 43 and TERPY in protein.

| Chelate | $\lambda_{exc}$[nm] | $\tau[\mu s]$ | $\epsilon \cdot \Phi$ |
|---|---|---|---|
| 34 | 328 | 1350 | 3860 |
| 42 | 315 | 2930 | 3770 |
| 43 | 310 | 2670 | 4050 |
| Tb$^{III}$(TERPY) in protein | 333 | 330 | 1170 |

Tb$^{III}$TERPY in protein: see Mukkala, V.-M., Takalo, H., Liitti, P. and Hemmilä, I., 1995, J. Alloys and Compounds 225, 507–510: compound 11 a.

EXAMPLE 51

The luminescence measurements of chelate-labelled antibodies.

The luminescence measurements of chelate-labelled antibodies were measured similarly as in Example 49 using appropriate dilutions of the conjugated proteins analyzed above.

EXAMPLE 52

Standard curve

A PSA standard curve where a PSA-antibody labelled with chelate 42 is used as a label. The curve is shown in FIG. 1.

It will be appreciated that the methods and compositions of the present invention can be incorporated in the form of a variety of embodiments, only a few of which are disclosed herein. It will be apparent to the skilled person that other embodiments exist and do not depart from the spirit of the invention. Thus, the described embodiments are illustrative and should not be construed as restrictive.

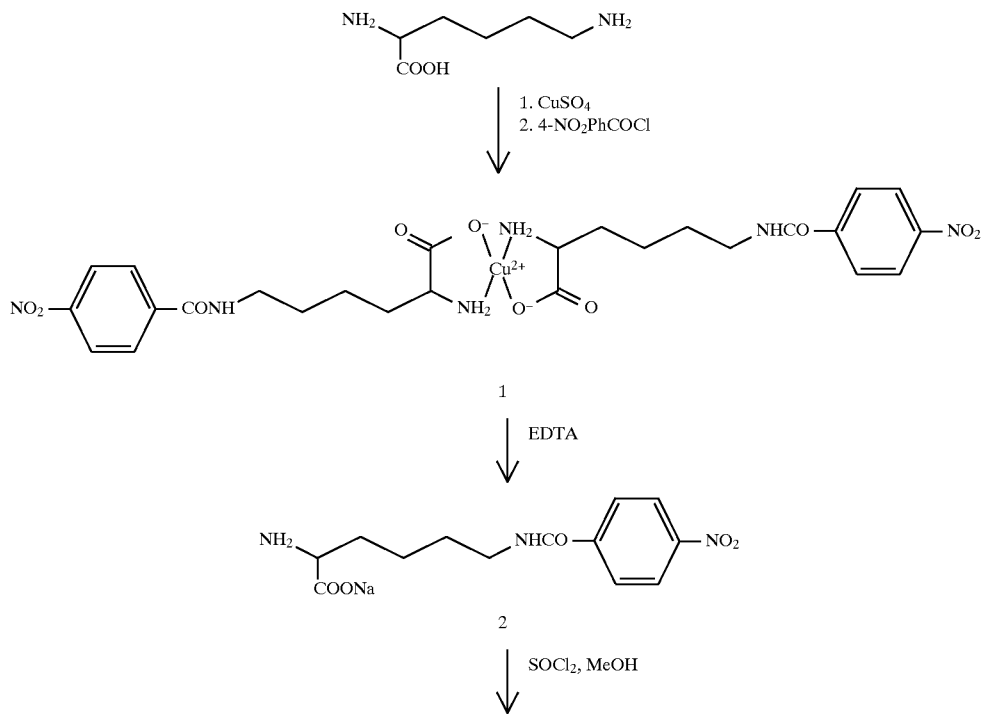

SCHEME 1.

-continued
SCHEME 1.
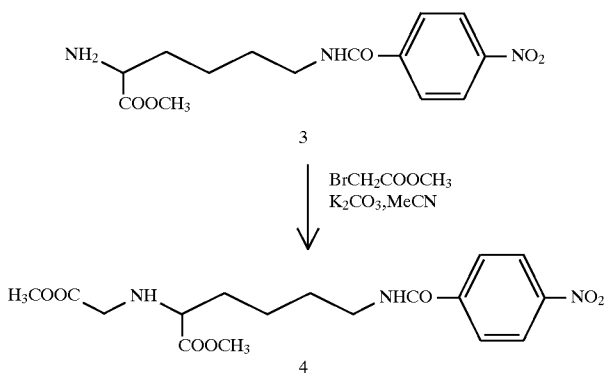
SCHEME 2.
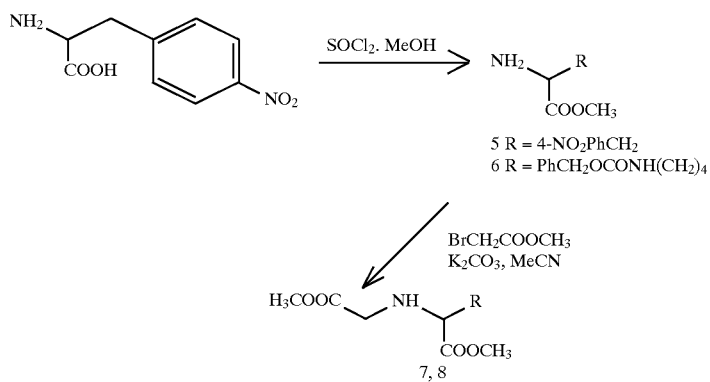
SCHEME 3.
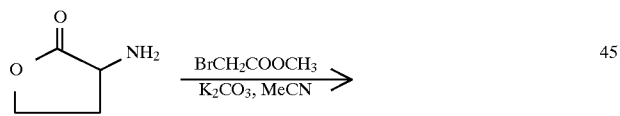
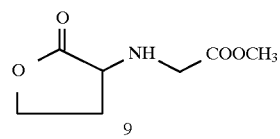
SCHEME 4.
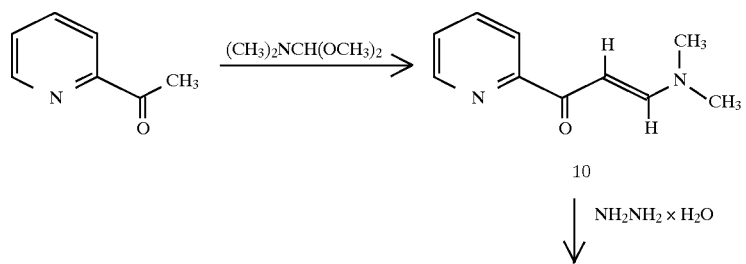

-continued
SCHEME 4.
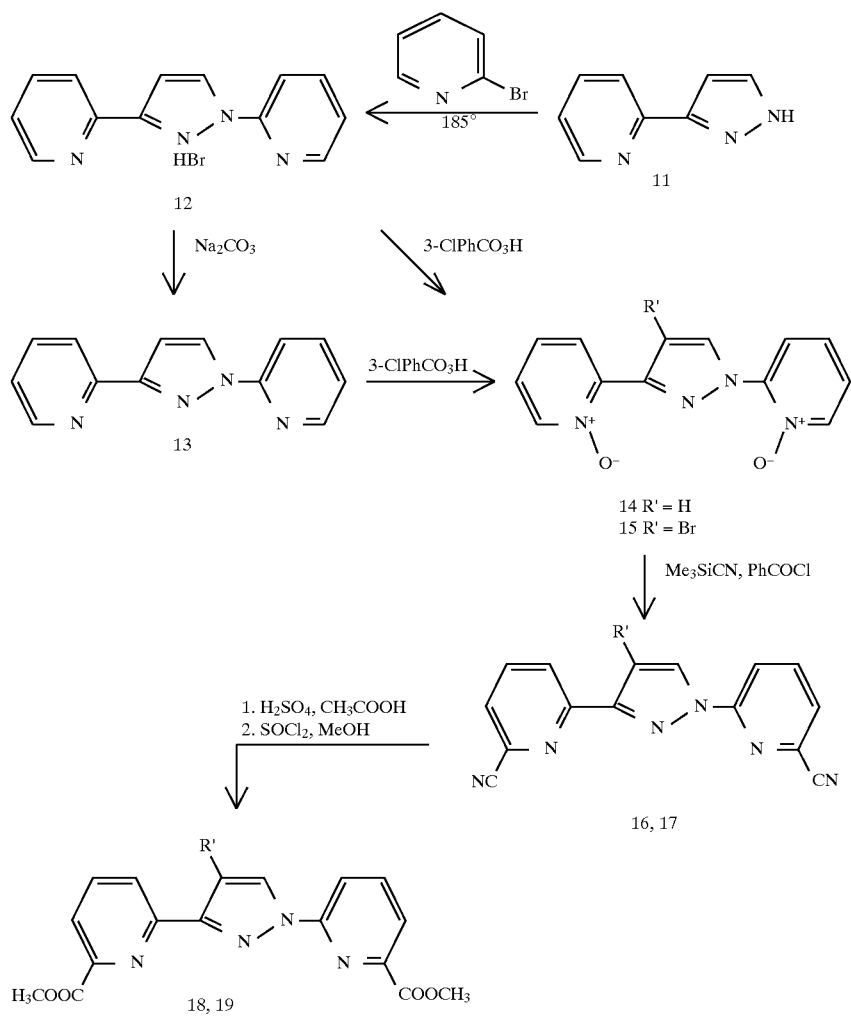
SCHEME 5.
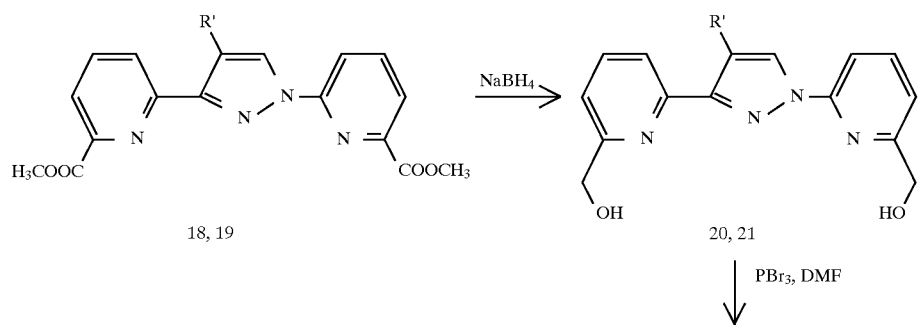

-continued
SCHEME 5.
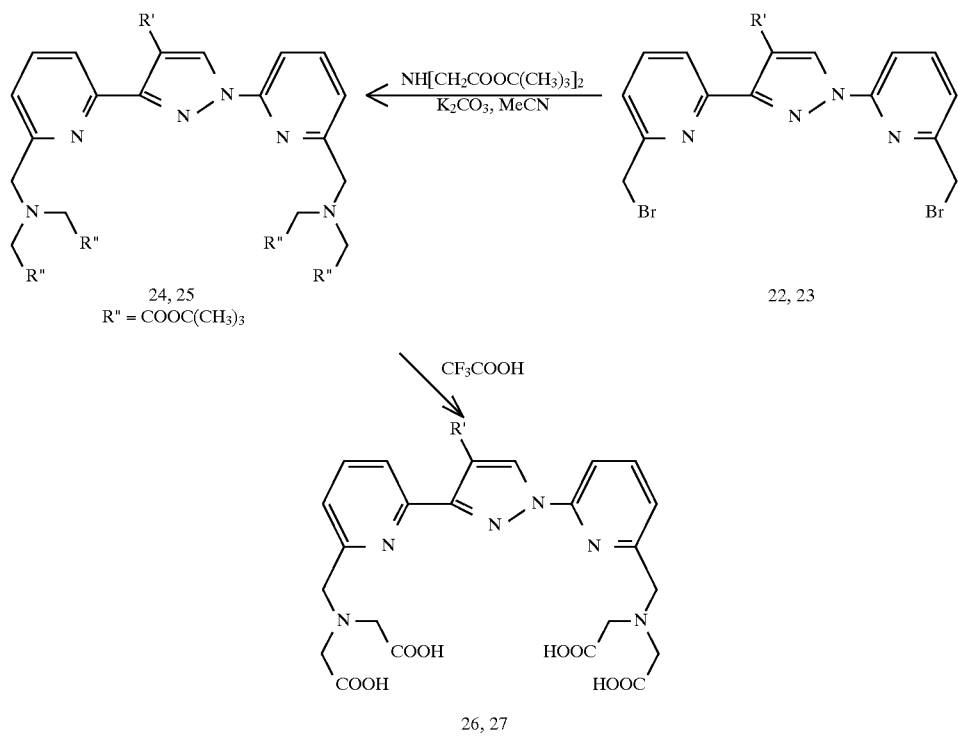
SCHEME 6.
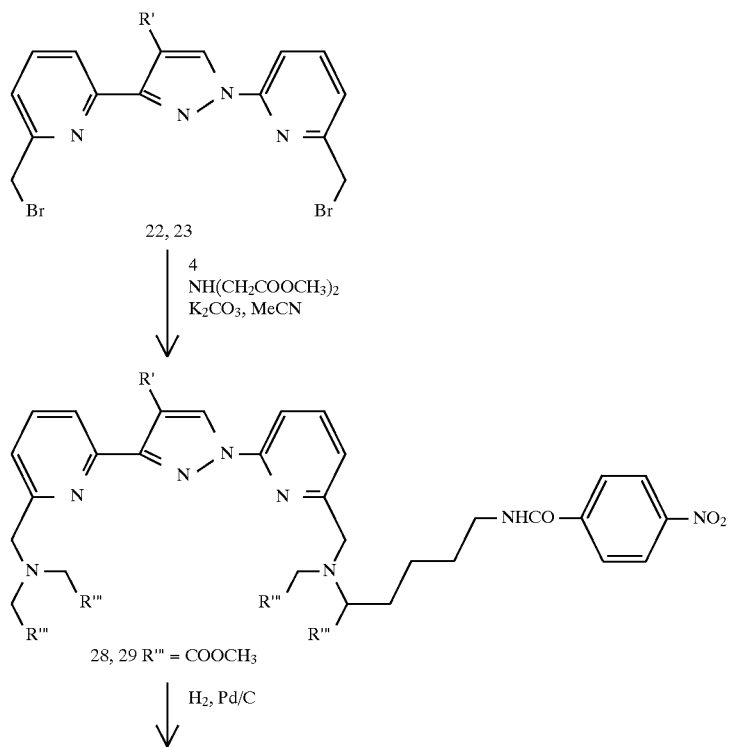

-continued
SCHEME 6.
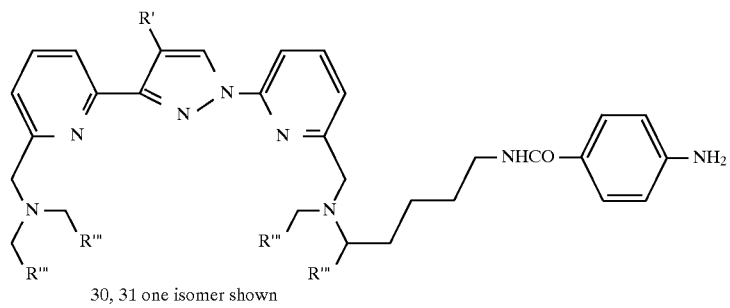
30, 31 one isomer shown
SCHEME 7.
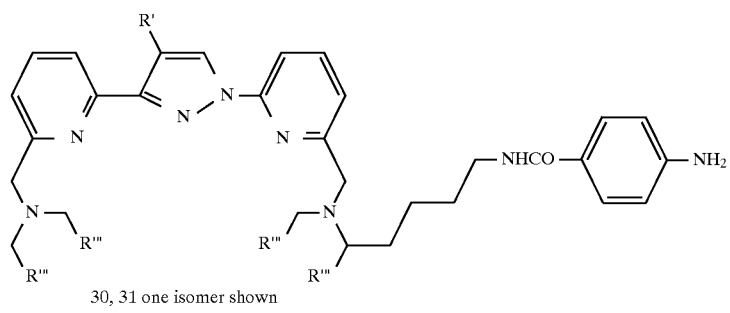
30, 31 one isomer shown
1. KOH, EtOH
2. TbCl₃
↓
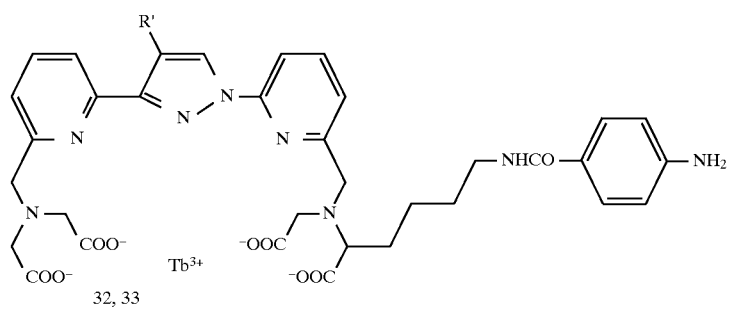
32, 33   Tb³⁺
$Cl_2C=S$ or 
↓

-continued
SCHEME 7.
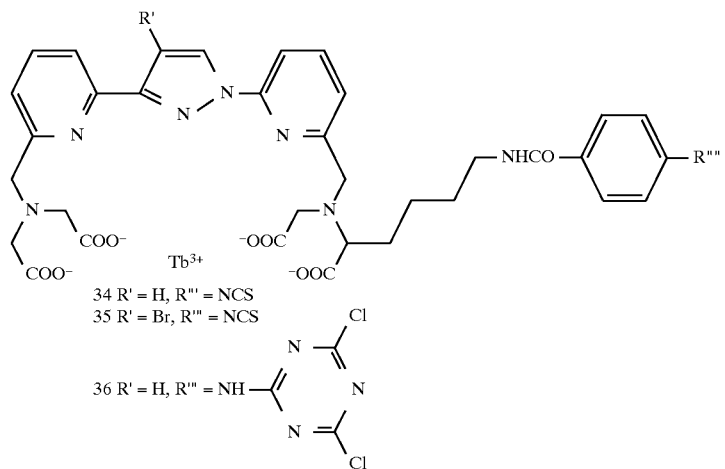
34 R' = H, R''' = NCS
35 R' = Br, R''' = NCS
36 R' = H, R''' = NH—[dichlorotriazinyl]
SCHEME 8.
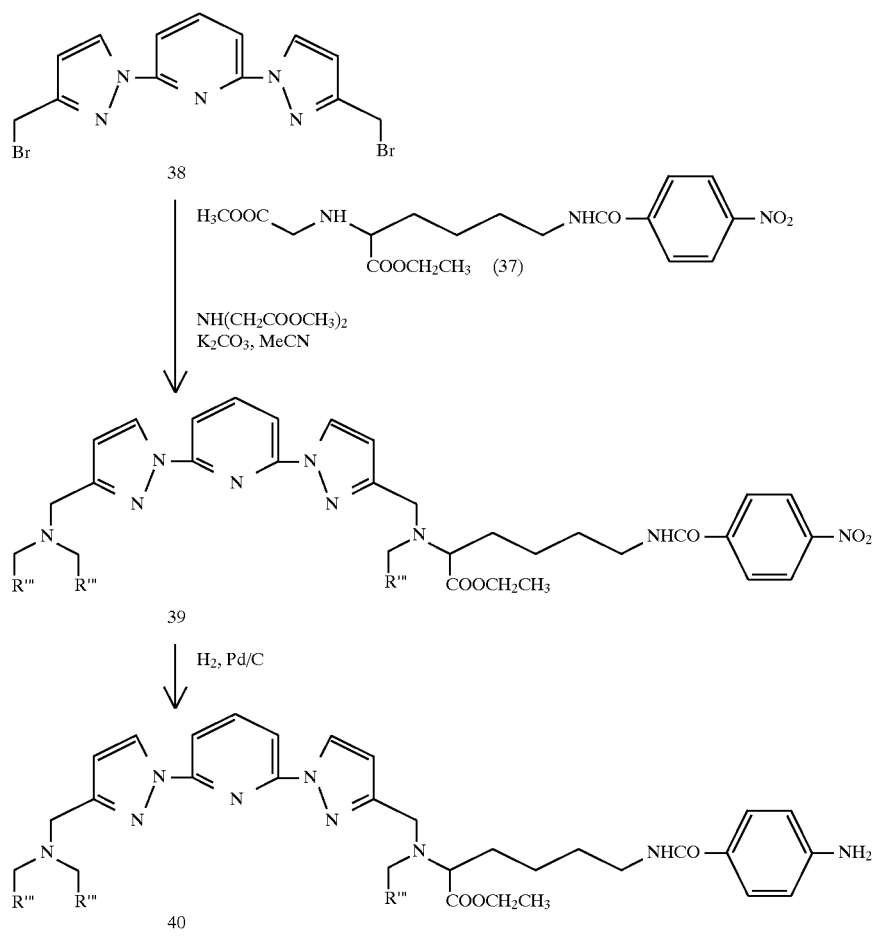

SCHEME 9.
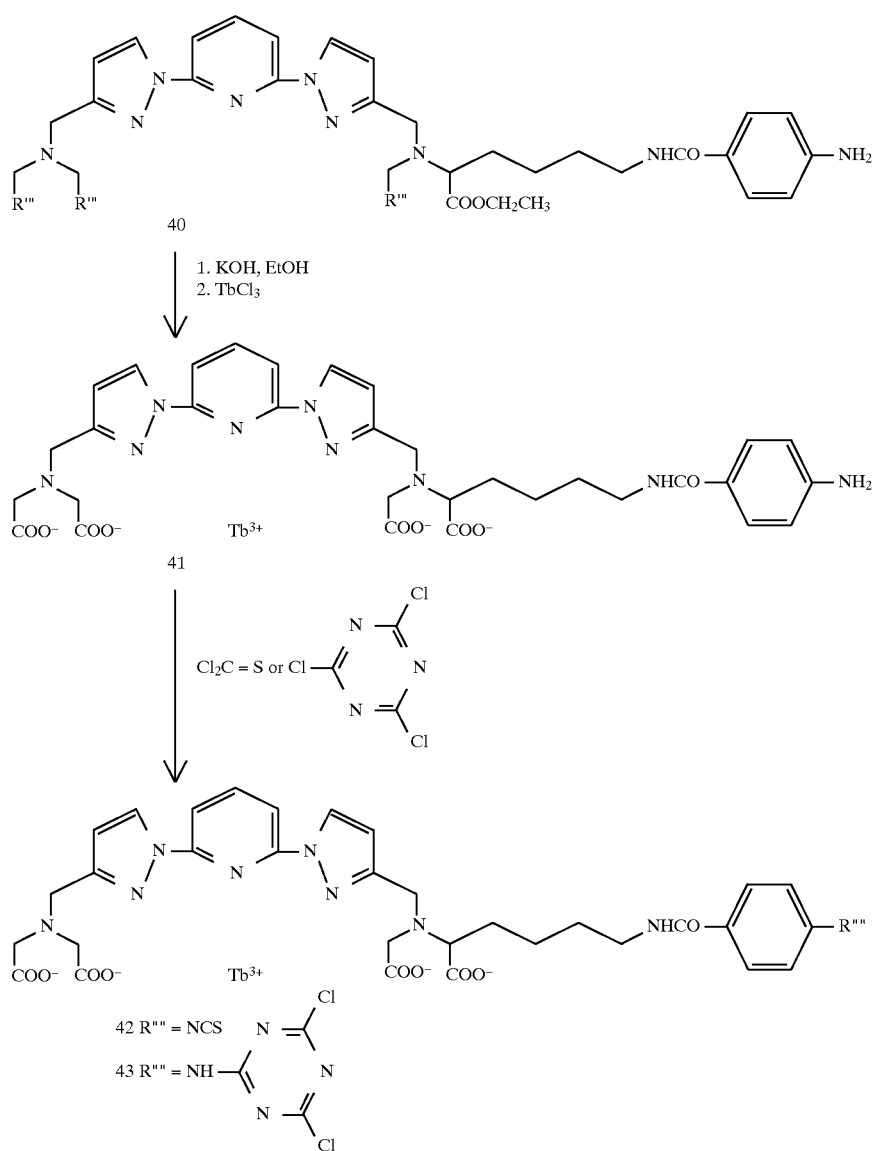
SCHEME 10.
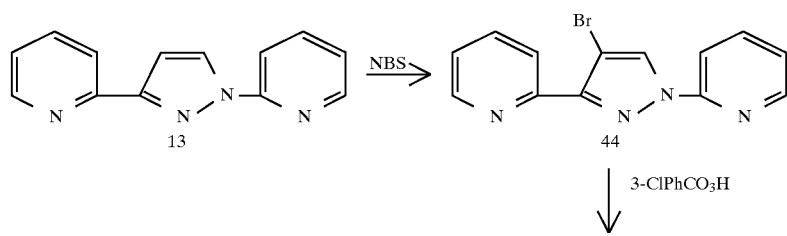

-continued
SCHEME 10.
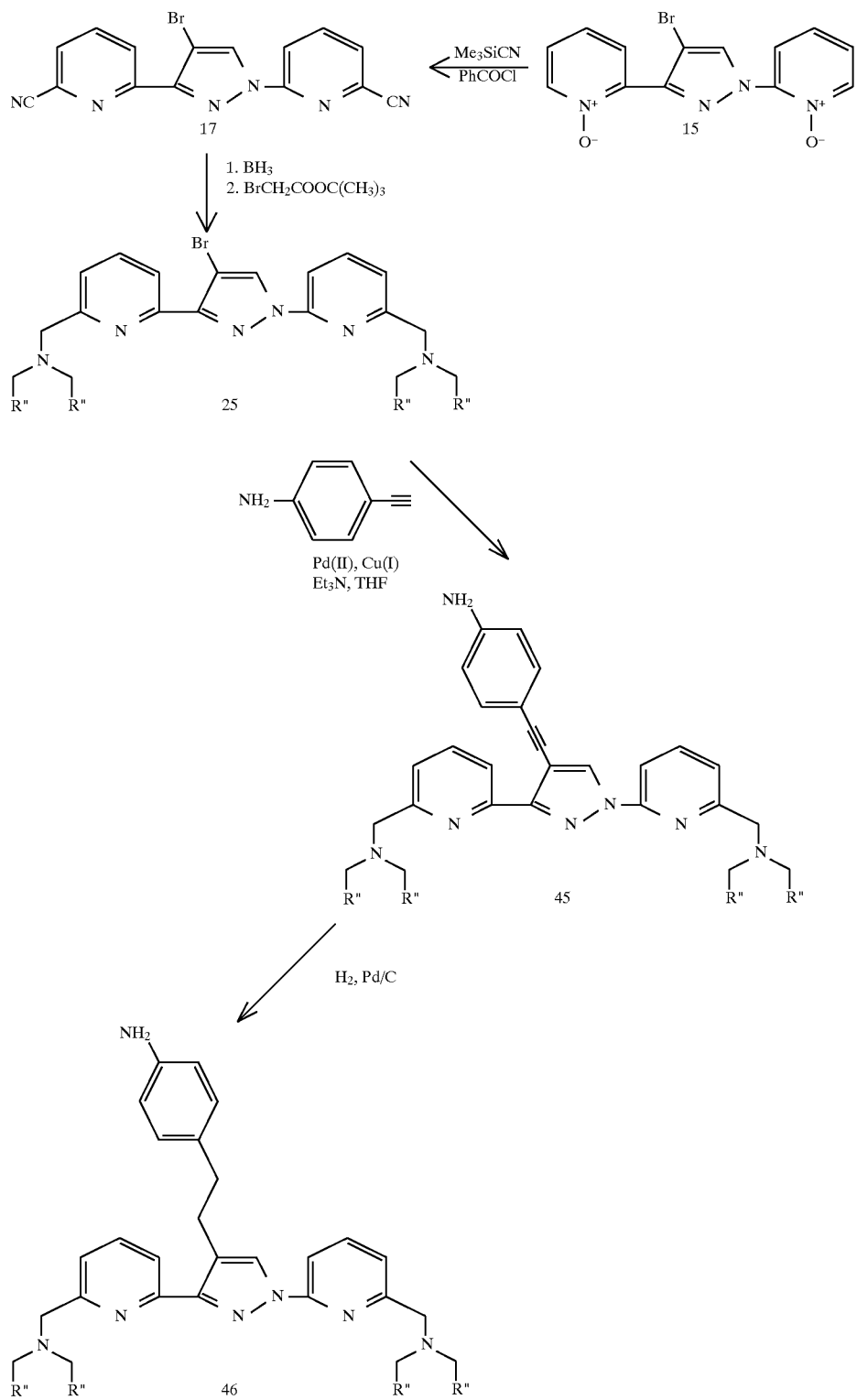

SCHEME 11.

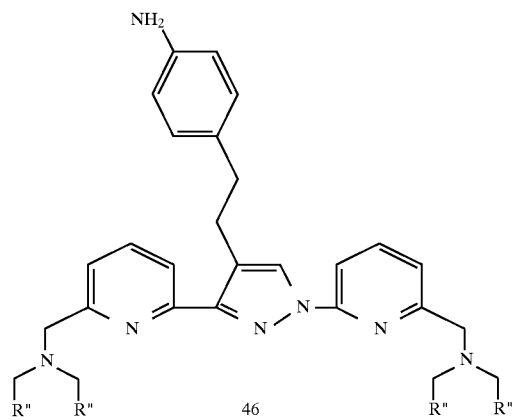

1. CF₃COOH
2. TbCl₃

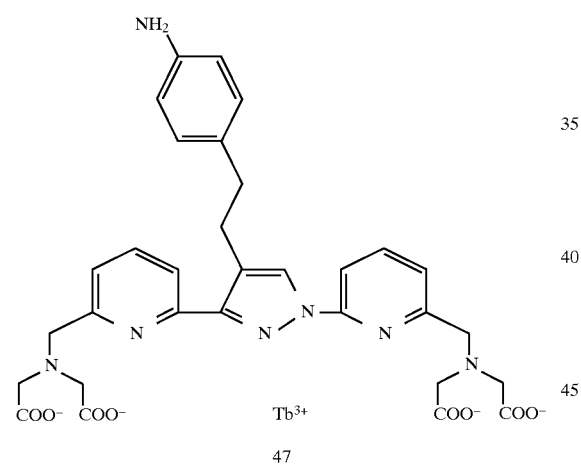

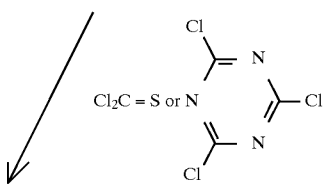

-continued
SCHEME 11.

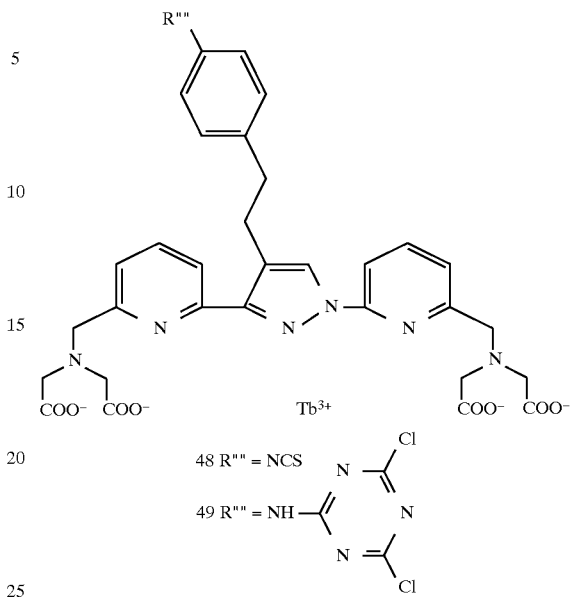

48 R"" = NCS

49 R"" = NH—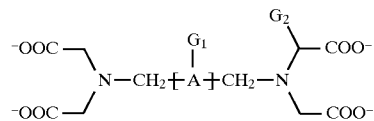

We claim:

1. A detectable molecule comprising a biospecific binding reactant attached to a luminescent lanthanide chelate comprising a lanthanide ion and a chelating ligand of the formula $$\begin{array}{c}\phantom{x}\\\text{-OOC}\diagdown\phantom{x}\phantom{x}\phantom{x}\phantom{x}\phantom{x}\phantom{x}\phantom{x}G_1\phantom{x}\phantom{x}\phantom{x}G_2\phantom{x}\phantom{x}\diagup\text{COO}^-\\\phantom{x}\phantom{x}\text{N}-\text{CH}_2+\text{A}+\text{CH}_2-\text{N}\\\text{-OOC}\diagup\phantom{x}\phantom{x}\phantom{x}\phantom{x}\phantom{x}\phantom{x}\phantom{x}\phantom{x}\phantom{x}\phantom{x}\phantom{x}\phantom{x}\phantom{x}\phantom{x}\phantom{x}\diagdown\text{COO}^-\end{array}$$

characterized in that a) —A— is a bivalent aromatic structure selected from the group consisting of

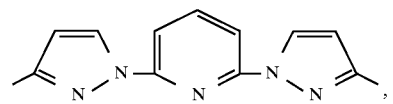,

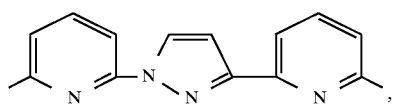, and

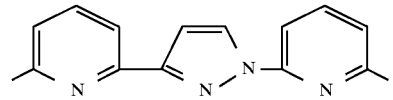

b) one of the groups $G_1$ to $G_2$ is selected from a group consisting of hydrogen, chloro, bromo, iodo, cyano, phenyl, alkyl and alkoxy, with the proviso that said alkyl contains 1–6 carbon atoms; and the other group $G_1$ or $G_2$ is a bridge which does not participate in the chelating process and which comprises one to four moieties, each moiety being selected from the group consisting of phenylene, alkylene containing 1–8 carbon atoms, ethynediyl (—C≡C—), ether (—O—), thioether (—S—) and amide (—CO—NH— and —NH—CO—);

and which is used for coupling to a biospecific binding reactant via thiourea (—NH—CS—NH—), aminoacetamide (—NH—CO—CH$_2$—NH—), amide (—NH—CO— and —CO—NH—), aliphatic thioether (—S—), disulfide (—S—S—) or 6-substituted-1,3,5-triazine-2,4-diamine; and c) the lanthanide ion is europium(III), terbium(III), dysprosium (III) or samarium (III).

2. The detectable molecule according to claim 1 characterized in that the biospecific binding reactant is selected from the group consisting of an antibody, an antigen, a receptor ligand, a specific binding protein, a DNA- or RNA-probe.

3. The detectable molecule according to claim 1 characterized in that the lanthanide chelate attached to a biospecific binding reactant is selected from the group consisting of
2- and 2"-[4-(4-isothiocyanatobenzamido)but-1-yl]-2,2',2",2"'-{[6,6'-(pyrazole-1",3"-diyl)bis(pyridine)-2,2'-diyl]bis(methylenenitrilo)}tetrakis(acetato) terbium(III),
2- and 2"-[4-(4-isothiocyanatobenzamido)but-1-yl]-2,2',2",2"'-{[6,6'-(pyrazole-1",3"-diyl)bis(pyridine)-2,2'-diyl]bis(methylenenitrilo)}tetrakis(acetato)terbium(III),
2- and 2"-{4-{4-[(4,6-dichloro-1,3,5-triazin-2-yl)amino]benzamido}but-1-yl}-2,2',2",2"'-{[6,6'-(pyrazole-1",3"-diyl)bis(pyridine)-2,2'-diyl]bis(methylenenitrilo)}tetrakis(acetato)terbium(III),
2-[4-(4-isothiocyanatobenzamido)but-1-yl]-2,2',2",2"'-{[1,1'-(pyridine-2",6"-diyl)bis(pyrazole)-3,3'-diyl]-bis(methylenenitrilo)}tetrakis(acetato)terbium(III),
2-{4-{4-[(4,6-dichloro-1,3,5-triazine-2-yl)amino]benzamido}but-1-yl}-2,2', 2",2"'-{[1,1'-(pyridine-2",6"-diyl)bis(pyrazole)-3,3'-diyl]bis(methylenenitrilo)}tetrakis(acetato)terbium(III),
2,2',2",2"'-{{6,6'-{4"-[2-(4-isothiocyanatophenyl)ethyl]pyrazole-1",3"-diyl}bis(pyridine)-2,2'-diyl}bis(methylenenitrilo)}tetrakis(acetato)terbium(III), and
2,2',2",2"'-{{6,6'-{4"-{2-[(4,6-dichloro-1,3,5-triazin-2-yl)amino]ethyl}pyrazole-1",3"-diyl}bis-(pyridine)-2,2'-diyl}bis(methylenenitrilo)}tetrakis(acetato)terbium(III).

4. A luminescent lanthanide chelate comprising a lanthanide ion and a chelating ligand of the formula

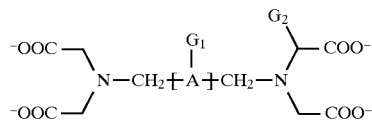

characterized in that a) —A— is a bivalent aromatic structure selected from the group consisting of

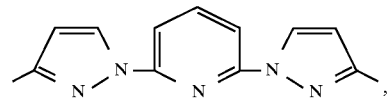

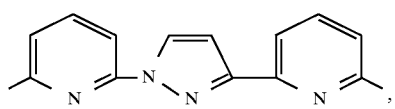

and

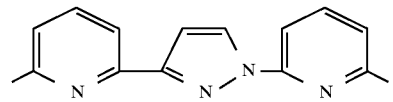

b) one of the groups $G_1$ or $G_2$ is selected from a group consisting of hydrogen, chloro, bromo, iodo, cyano, phenyl, alkyl and alkoxy, with the proviso that said alkyl contains 1–6 carbon atoms; and the other group $G_1$ or $G_2$ is a substituent which does not participate in the chelating process, which comprises one to four moieties, each moiety being selected from the group consisting of phenylene, alkylene containing 1–8 carbon atoms, ethynediyl (—C≡C—), ether (—O—), thioether (—S—) and amide (—CO—NH— and —NH—CO—), which additionally contains one moiety selected from a group containing hydroxy, nitro, amino, aminooxy, carboxyl, aldehyde or mercapto groups or an activated form made from them such as isocyanato, isothiocyanato, diazonium, bromoacetamido, iodoacetamido, reactive esters, pyridyl-2-dithio or 6-substituted 4-chloro-1,3,5-triazon-2-ylamino;

and which is used for coupling to a biospecific binding reactant; and c) the lanthanide ion is europium(III), terbium(III), dysprosium (III) or samarium (III).

5. The lanthanide chelate according to claim 4 characterized in that the chelating ligand is selected from the group consisting of
2- and 2"-[4-(4-isothiocyanatobenzamido)but-1-yl]-2,2',2",2"'-{[6,6'-(pyrazole-1",3"-diyl)bis(pyridine)-2,2'-diyl]bis(methylenenitrilo)}tetrakis(acetato) terbium(III),
2- and 2"-[4-(4-isothiocyanatobenzamido)but-1-yl]-2,2',2",2"'-{[6,6'-(pyrazole-1",3"-diyl)bis(pyridine)-2,2'-diyl]bis(methylenenitrilo)}tetrakis(acetato)terbium(III),
2- and 2"-{4-{4-[(4,6-dichloro-1,3,5-triazin-2-yl)amino]benzamido}but-1-yl}-2,2',2",2"'-{[6,6'-(pyrazole-1",3"-diyl)bis(pyridine)-2,2'-diyl]bis(methylenenitrilo)}tetrakis(acetato)terbium(III),
2-[4-(4-isothiocyanatobenzamido)but-1-yl]-2,2',2",2"'-{[1,1'-(pyridine-2",6"-diyl)bis(pyrazole)-3,3'-diyl]-bis(methylenenitrilo)}tetrakis(acetato)terbium(III),
2-{4-{4-[(4,6-dichloro-1,3,5-triazine-2-yl)amino]benzamido}but-1-yl}-2,2', 2",2"'-{[1,1'-(pyridine-2",6"-diyl)bis(pyrazole)-3,3'-diyl]bis(methylenenitrilo)}tetrakis(acetato)terbium(III),
2,2',2",2"'-{{6,6'-{4"-[2-(4-isothiocyanatophenyl)ethyl]pyrazole-1",3"-diyl}bis(pyridine)-2,2'-diyl}bis(methylenenitrilo)}tetrakis(acetato)terbium(III), and
2,2',2",2"'-{{6,6'-{4"-{2-[(4,6-dichloro-1,3,5-triazin-2-yl)amino]ethyl}pyrazole-1",3"-diyl}bis-(pyridine)-2,2'-diyl}bis(methylenenitrilo)}tetrakis(acetato)terbium(III).

6. A method of carrying out a biospecific binding assay, comprising binding a detectable molecule to an analyte to be determined, said detectable molecule comprising a biospecific binding reactant attached to a luminescent lanthanide chelate comprising lanthanide ion and a chelating ligand of the formula

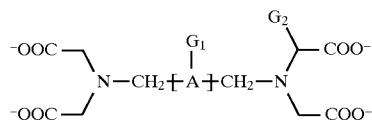

characterized in that
a) —A— is a bivalent aromatic structure selected from the group consisting of

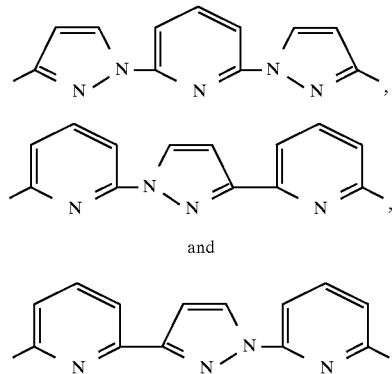

b) one of the groups $G_1$ or $G_2$ is selected from a group consisting of hydrogen, chloro, bromo, iodo, cyano, phenyl, alkyl and alkoxy, with the proviso that said alkyl contains 1–6 carbon atoms; and the other group $G_1$ or $G_2$ is a bridge which does not participate in the chelating process and which comprises one to four moieties, each moiety being selected from the group consisting of phenylene, alkylene containing 1–8 carbon atoms, ethynediyl (—C≡C—), ether (—O—), thioether (—S—) and amide (—CO—NH— and —NH—CO—);

and which is used for coupling to the biospecific binding reactant via thiourea (—NH—CS—NH—), aminoacetamide (—NH—CO—$CH_2$—NH—), amide (—NH—CO— and —CO—NH—), aliphatic thioether (—S—), disulfide (—S—S—) or 6-substituted-1,3,5-triazine-2, 4-diamine; and c) the lanthanide ion is europium(III), terbium(III), dysprosium (III) or samarium (III).

7. The method according to claim 6 characterized in that the biospecific binding reactant is selected from the group consisting of an antibody, antigen, receptor ligand, a specific binding protein, a DNA- or RNA-probe.

8. The method according to claim 6 characterized in that the lanthanide chelate attached to a biospecific binding reactant is selected from the group consisting of 2- and 2"-[4-(4-isothiocyanatobenzamido)but-1-yl]-2,2',2", 2'''-{[6,6'-(pyrazole-1",3"-diyl)bis(pyridine)-2,2'-diyl]bis(methylenenitrilo)}tetrakis(acetato) terbium(III), 2- and 2"-[4-(4-isothiocyanatobenzamido)but-1-yl]-2,2',2", 2'''-{[6,6'-(pyrazole-1",3"-diyl)bis(pyridine)-2,2'-diyl]bis(methylenenitrilo)}tetrakis(acetato)terbium(III), 2- and 2"-{4-{4-[(4,6-dichloro-1,3,5-triazin-2-yl)amino]benzamido}but-1-yl}-2,2',2",2'''-{[6,6'-(pyrazole-1",3"-diyl)bis(pyridine)-2,2'-diyl]bis(methylenenitrilo)}tetrakis(acetato)terbium(III), 2-[4-(4-isothiocyanatobenzamido)but-1-yl]-2,2',2",2'''-{[1,1'-(pyridine-2",6"-diyl)bis(pyrazole)-3,3'-diyl]-bis(methylenenitrilo)}tetrakis(acetato)terbium(III), 2-{4-{4-[(4,6-dichloro-1,3,5-triazine-2-yl)amino]benzamido}but-1-yl}-2,2', 2",2'''-{[1,1'-(pyridine-2",6"-diyl)bis(pyrazole)-3,3'-diyl]bis(methylenenitrilo)}tetrakis(acetato)terbium(III), 2,2',2",2'''-{{6,6'-{4"-[2-(4-isothiocyanatophenyl)ethyl]pyrazole-1",3"-diyl}bis(pyridine)-2,2'-diyl}bis(methylenenitrilo)}tetrakis(acetato)terbium(III), and 2,2',2",2'''-{{6,6'-{4"-{2-[(4,6-dichloro-1,3,5-triazin-2-yl)amino]ethyl}pyrazole-1",3"-diyl}bis-(pyridine)-2,2'-diyl}bis(methylenenitrilo)}tetrakis(acetato)terbium(III).

\* \* \* \* \*